(12) United States Patent
Klappert et al.

(10) Patent No.: US 10,271,087 B2
(45) Date of Patent: Apr. 23, 2019

(54) METHODS AND SYSTEMS FOR MONITORING ATTENTIVENESS OF A USER BASED ON BRAIN ACTIVITY

(71) Applicant: Rovi Guides, Inc., San Carlos, CA (US)

(72) Inventors: Walter R. Klappert, Los Angeles, CA (US); Michael R. Nichols, La Canada Flintridge, CA (US); Camron Shimy, Canyon Country, CA (US); William Wagner, Chester Springs, PA (US); Yinghsueh (Annie) Chen, San Gabriel, CA (US); Paul T. Stathacopoulos, San Carlos, CA (US)

(73) Assignee: Rovi Guides, Inc., San Jose, CA (US)

( * ) Notice: Subject to any disclaimer, the term of this patent is extended or adjusted under 35 U.S.C. 154(b) by 0 days.

(21) Appl. No.: 14/038,171

(22) Filed: Sep. 26, 2013

(65) Prior Publication Data
US 2015/0033245 A1  Jan. 29, 2015

Related U.S. Application Data

(60) Provisional application No. 61/857,749, filed on Jul. 24, 2013.

(51) Int. Cl.
*H04H 60/56* (2008.01)
*H04N 21/422* (2011.01)
(Continued)

(52) U.S. Cl.
CPC ..... *H04N 21/42201* (2013.01); *A61B 5/0476* (2013.01); *A61B 5/0482* (2013.01); *A61B 5/0488* (2013.01); *A61B 5/0496* (2013.01); *A61B 5/1103* (2013.01); *G06F 3/015* (2013.01); *H04N 21/4126* (2013.01); *H04N 21/42206* (2013.01); *H04N 21/42222* (2013.01); *H04N 21/4314* (2013.01); *H04N 21/4316* (2013.01);
(Continued)

(58) Field of Classification Search
None
See application file for complete search history.

(56) References Cited

U.S. PATENT DOCUMENTS 4,955,388 A   9/1990  Silberstein
5,649,061 A * 7/1997  Smyth .................... A61B 3/113
                                                     250/221

(Continued)

OTHER PUBLICATIONS

Kastelein, "NeuroSky, Brain-Computer Interface Technologies," Published Nov. 11, 2013 (downloaded Nov. 15, 2013, http://technode.com/2011/08/18/world%E2%80%99s-first-brain-controlled-smart-tv-powered-by-neurosky/).

(Continued)

*Primary Examiner* — Samira Monshi
(74) *Attorney, Agent, or Firm* — Haley Guiliano LLP

(57) ABSTRACT

Methods and systems are disclosed herein for a media guidance application configured to monitor attentiveness of a user based on the brain activity of the user. For example, a media guidance application may monitor brain activity associated with an attentiveness level of the user and in response to determining the attentiveness level of the user does not correspond to the threshold attentiveness level, perform an operation associated with a low attentiveness level of the user (e.g., performing a scan operation through various content providers).

18 Claims, 20 Drawing Sheets

(51) Int. Cl.

| | | |
|---|---|---|
| G06F 3/01 | (2006.01) | |
| A61B 5/0476 | (2006.01) | |
| H04N 21/431 | (2011.01) | |
| H04N 21/482 | (2011.01) | |
| A61B 5/0488 | (2006.01) | |
| A61B 5/0496 | (2006.01) | |
| H04N 21/442 | (2011.01) | |
| A61B 5/0482 | (2006.01) | |
| A61B 5/11 | (2006.01) | |
| H04N 21/466 | (2011.01) | |
| H04N 21/41 | (2011.01) | |
| H04N 21/433 | (2011.01) | |
| H04N 21/443 | (2011.01) | |
| H04N 21/485 | (2011.01) | |
| A61B 5/00 | (2006.01) | |

(52) U.S. Cl.
CPC ..... *H04N 21/4333* (2013.01); *H04N 21/4334* (2013.01); *H04N 21/4436* (2013.01); *H04N 21/44218* (2013.01); *H04N 21/4668* (2013.01); *H04N 21/482* (2013.01); *H04N 21/4852* (2013.01); *A61B 5/486* (2013.01); *A61B 5/6803* (2013.01); *A61B 5/7246* (2013.01); *A61B 5/7264* (2013.01)

(56) References Cited

U.S. PATENT DOCUMENTS

| | | | |
|---|---|---|---|
| 6,239,794 B1 | 5/2001 | Yuen et al. | |
| 6,388,714 B1 | 5/2002 | Schein et al. | |
| 6,564,378 B1 | 5/2003 | Satterfield et al. | |
| 6,605,038 B1 | 8/2003 | Teller et al. | |
| 6,756,997 B1 | 6/2004 | Ward, III et al. | |
| 7,165,098 B1 | 1/2007 | Boyer et al. | |
| 7,245,273 B2 | 7/2007 | Eberl et al. | |
| 7,693,869 B2 | 4/2010 | Hutson et al. | |
| 7,761,892 B2 | 7/2010 | Ellis et al. | |
| 7,818,395 B2 | 10/2010 | Pizano | |
| 8,046,801 B2 | 10/2011 | Ellis et al. | |
| 8,285,223 B2 | 10/2012 | Unger | |
| 8,332,883 B2 | 12/2012 | Lee et al. | |
| 8,373,768 B2 | 2/2013 | Bill | |
| 8,392,250 B2 | 3/2013 | Pradeep et al. | |
| 8,418,193 B2 | 4/2013 | Saito et al. | |
| 8,676,230 B2 | 3/2014 | Alexander et al. | |
| 8,902,045 B1 | 12/2014 | Linn et al. | |
| 9,367,131 B2 | 6/2016 | Klappert et al. | |
| 9,531,708 B2 | 12/2016 | Cornell et al. | |
| 2002/0029385 A1* | 3/2002 | Moir | H04N 5/44543 725/53 |
| 2002/0162031 A1 | 10/2002 | Levin et al. | |
| 2002/0174430 A1 | 11/2002 | Ellis et al. | |
| 2003/0110499 A1 | 6/2003 | Knudson et al. | |
| 2005/0251827 A1 | 11/2005 | Ellis et al. | |
| 2005/0285747 A1 | 12/2005 | Kozlay | |
| 2005/0289058 A1 | 12/2005 | Hoffman et al. | |
| 2006/0106734 A1 | 5/2006 | Hoffman et al. | |
| 2006/0142968 A1 | 6/2006 | Han et al. | |
| 2007/0025311 A1 | 2/2007 | Jeong et al. | |
| 2007/0050636 A1 | 3/2007 | Menczel | |
| 2008/0177197 A1 | 7/2008 | Lee et al. | |
| 2009/0023422 A1 | 1/2009 | MacInnis et al. | |
| 2009/0083850 A1 | 3/2009 | Fadell et al. | |
| 2009/0089833 A1 | 4/2009 | Saito et al. | |
| 2009/0150919 A1* | 6/2009 | Lee et al. | 725/10 |
| 2009/0214060 A1 | 8/2009 | Chuang et al. | |
| 2010/0153885 A1 | 6/2010 | Yates | |
| 2010/0169905 A1* | 7/2010 | Fukuchi | H04N 21/4223 725/10 |
| 2010/0199299 A1* | 8/2010 | Chang | H04N 7/17318 725/32 |
| 2010/0249636 A1 | 9/2010 | Pradeep et al. | |
| 2010/0291963 A1 | 11/2010 | Patel et al. | |
| 2011/0015469 A1* | 1/2011 | Walter | A61M 21/02 600/27 |
| 2011/0045803 A1 | 2/2011 | Kim | |
| 2011/0077548 A1* | 3/2011 | Torch | A61B 3/112 600/558 |
| 2011/0134026 A1 | 6/2011 | Kang et al. | |
| 2011/0209214 A1 | 8/2011 | Simske et al. | |
| 2012/0029322 A1 | 2/2012 | Wartena et al. | |
| 2012/0078820 A1 | 3/2012 | Azam | |
| 2012/0090003 A1 | 4/2012 | Dove et al. | |
| 2012/0197737 A1 | 8/2012 | LeBoeuf et al. | |
| 2012/0295589 A1 | 11/2012 | Alexander et al. | |
| 2013/0012829 A1* | 1/2013 | Jo | 600/544 |
| 2013/0063550 A1 | 3/2013 | Ritchey et al. | |
| 2013/0109995 A1 | 5/2013 | Rothman et al. | |
| 2013/0113628 A1* | 5/2013 | Shepherd | A61B 5/0476 340/573.1 |
| 2013/0133055 A1 | 5/2013 | Shirook et al. | |
| 2013/0179087 A1 | 7/2013 | Carripoli | |
| 2013/0205311 A1 | 8/2013 | Ramaswamy et al. | |
| 2014/0033322 A1 | 1/2014 | Nair et al. | |
| 2014/0059695 A1 | 2/2014 | Parecki et al. | |
| 2014/0068723 A1 | 3/2014 | Grim | |
| 2014/0089673 A1 | 3/2014 | Luna | |
| 2014/0096152 A1 | 4/2014 | Ferens et al. | |
| 2014/0098116 A1* | 4/2014 | Baldwin | 345/522 |
| 2014/0109142 A1 | 4/2014 | van Copenolle et al. | |
| 2014/0126877 A1 | 5/2014 | Crawford et al. | |
| 2014/0169596 A1 | 6/2014 | Lunner et al. | |
| 2014/0201767 A1 | 7/2014 | Seiden et al. | |
| 2014/0223462 A1 | 8/2014 | Aimone et al. | |
| 2014/0282945 A1 | 9/2014 | Smith | |
| 2015/0002387 A1 | 1/2015 | Cai et al. | |
| 2015/0012950 A1 | 1/2015 | Corl | |
| 2015/0029087 A1 | 1/2015 | Klappert et al. | |
| 2015/0033258 A1 | 1/2015 | Klappert et al. | |
| 2015/0033259 A1 | 1/2015 | Klappert et al. | |
| 2015/0033266 A1 | 1/2015 | Klappert et al. | |
| 2015/0150074 A1 | 5/2015 | Nolan et al. | |
| 2015/0261946 A1 | 9/2015 | Yoon et al. | |
| 2016/0366462 A1 | 12/2016 | Klappert et al. | |
| 2016/0371721 A1 | 12/2016 | Bogdon | |

OTHER PUBLICATIONS

Lim, "World's First Brain-Controlled Smart TV Powered by NeuroSky," Published Aug. 11, 2011 (downloaded Nov. 15, 2013, http://www.appmarket.tv/transmedia/2343-neurosky-company-behind-brain-powered-tv-brings-its-smart-sensors-to-new-verticals.html?utm_source=TV+App+Market+Newsletter).

Wyczesany, Miroslaw et al., "Subjective mood estimation co-varies with spectral power EEG characteristics," Department of Psychophysiology, Jagiellonian University, Krakow, Poland, Acta Neurobiol Exp, 68: 180-192, 2008.

Tan, Bao Hong, Using a Low-cost EEG Sensor to Detect Mental States, CMU-CS-12-134, School of Computer Science, Carnegie Mellon University, Aug. 2012.

Hamadicharef et al., "Learning EEG-based Spectral-Spatial Patterns for Attention Level Measurement," Institute for Infocomm Research, 2009.

Bos, Danny Oude, "EEG-based Emotion Recognition, The Influence of Visual and Auditory Stimuli," Department of Computer Science, University of Twente, 2006.

Frank et al., "Biofeedback in medicine: who, when, why and how?" Ment. Health Fam. Med., Jun. 2010.

Yamasaki et al., "Dissociable prefrontal brain systems for attention and emotion," PNAS, vol. 99, No. 17, 2002.

International Search Report and Written Opinion for PCT/US2014/046125 dated Sep. 22, 2014.

Business Wire (Emotiv Unveils World's First Brain-Controlled Video Gaming Headset, 2008, Web, Retrieved from: http://www.businesswire.com/home/20080220005408/en/Emotiv-Unveils-Worlds-Brain-Controlled-Video-Gaming-Headset).

(56) References Cited

OTHER PUBLICATIONS

Stevens et al. (Entertainment Computing—ICEC 2008, 7th International Conference Proceedings, Pittsburgh, PA, USA, p. 227).
Emotiv (P3-P4 and midline, 2010, Web, Retrieved from: https://www.gmotiv.com/forums/topic/P3_P4_and_midline/)
Michel et al (Localization of the sources of EEG delta, theta, alpha and beta frequency bands using the FFT dipole approximation, 1992, Electroencephalogr Clin Neurophysio., 82(1):38-44).
Emotivstation (Use of the Emotiv Epoc headset, 2011, Web Video, Retrieved from: https://www.youtube.com/watch?v+OQ8sgKc6518).
Ekanayake (Research Use of Emotiv EPOC, 2011, Web, Retrieved from: http://neurofeedback.visaduma.info/emotivresearch_o.htm).
Emotiv (EEG meditation with Emotiv EPOC Research, 2011, Web, Retrieved from: https://www.emotiv.com/forums/topic/EEG_meditation_Emotiv_Epoc_Research_Warp_5/).
Emotiv (Electrodes locations questions, 2011, Web, Retrieved from: https://www.emotiv.com/forums/topic/Electrodes_locations_questions/).
Rybak, "Frontal Alpha Power Asymmetry in Aggressive Children and Adolescents With Mood and Disruptive Behavior Disorders," Clinical EEG and Neuroscience, 37(1):16-24 (2006).
Zhukov et al., Independent Component Analysis for EEG Source Localization in Realistic Head Models, 2000, IEEE Engineering in Medicine and Biology Magazine, pp. 1-10).

\* cited by examiner

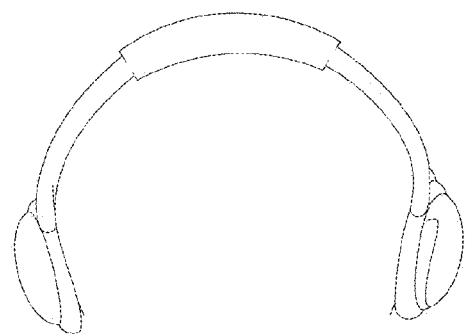
600
630
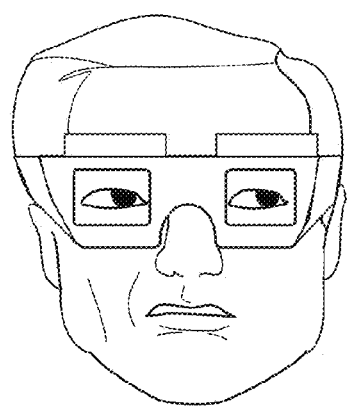
660
FIG. 6

900

902
Monitor brain activity of a user for a first brain state, in which the first brain state is associated with performing a first operation of a media guidance application

904
Generate for display an icon on a display screen, in which the icon provides feedback to the user related to achieving the first brain state

906
In response to detecting a change in the brain activity of the user, adjust the icon on the display screen to reflect the change in the brain activity of the user

FIG. 9

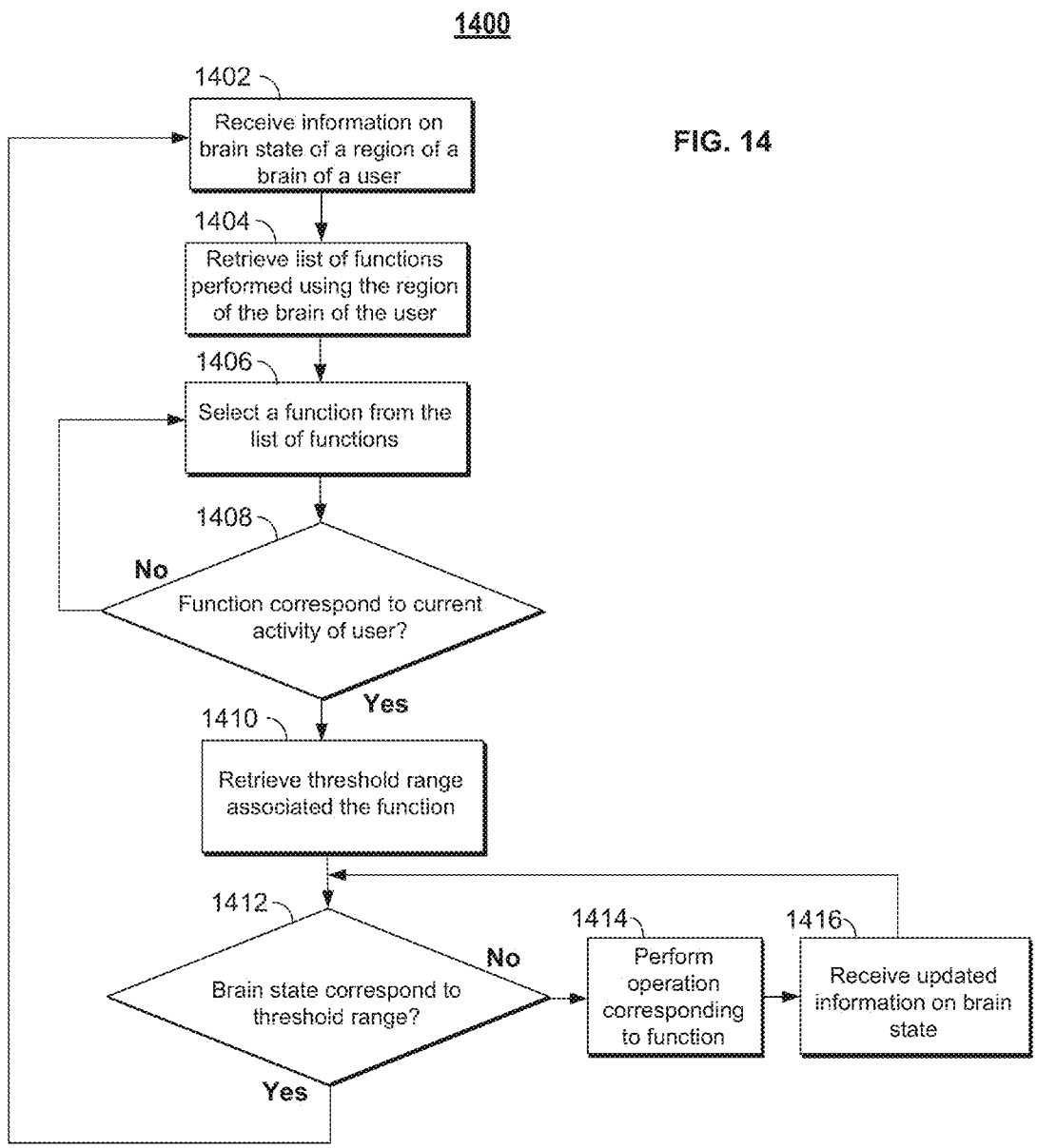

1500

1502
Receive a user request to monitor brain activity of a user with a user device, in which the user device operates in a first mode and a second mode, and wherein the first mode is associated with a first power consumption level and the second mode is associated with a second power consumption level

1504
In response to the user request, monitor the brain activity of the user with the user device in the first mode

1506
In response to detecting the brain activity of the user does not correspond to threshold range, change from the first mode to the second mode and monitor the brain activity of the user with the user device in the second mode

FIG. 15

METHODS AND SYSTEMS FOR MONITORING ATTENTIVENESS OF A USER BASED ON BRAIN ACTIVITY

CROSS-REFERENCE TO RELATED APPLICATIONS

This application claims the benefit of U.S. provisional patent application No. 61/857,749, filed Jul. 24, 2013, which is hereby incorporated by reference in its entirety.

BACKGROUND

In conventional systems, consumers of media have a plethora of content options available. For example, the rise in content available via cable, satellite, on-demand, and/or Internet systems provides users with ever increasing amounts of content options. Moreover, as the types of devices on which users may access this media changes, conventional methods (e.g., handheld remote controls, touchscreen interfaces, etc.) may no longer meet all of the users needs. For example, a small display screen (e.g., common with many mobile devices), with spatial limits for the amount of content that may be displayed, may reduce the efficiency at which a user may search and access media.

SUMMARY

Accordingly, method and systems are disclosed herein for a media guidance application configured to monitor brain activity in order to navigate, recommend, provide access to, and perform operations related to media content. By monitoring brain activity, in contrast to relying on one or more convention user input types (e.g., handheld remote controls, physical buttons, touchscreen interfaces, etc.), a media guidance application as disclosed herein may more intuitively and more efficiently meet the needs of a user.

For example, as described herein a media guidance application configured to monitor brain activity may perform various functions, including, but not limited to, recommending media assets that correspond to a mood of a user (or induce a preferred mood), providing on-screen options that display or provide access to operations without the need for a user to interact with the options via conventional means, monitoring the attentiveness of a user, compensating for unusual brain activity in distinct areas of the brain, adjusting power levels in a user device based on the brain activity of a user, and/or any combinations thereof. Furthermore, the method and systems described herein may be applied to a vast array of social and scientific fields such as advertising, personal/commercial entertainment, and/or medical therapy.

In some aspects, the media guidance application (or a user device upon which the media guidance application is implemented) may incorporate and/or have access to an electroencephalogram unit ("EEG") indicating a first frequency range of voltage fluctuations in the brain activity of a user and/or an electromyogram unit ("EMG") indicating first electrical activity of muscles near a brain of the user at rest and during contraction. For example, an EMG may indicate (by detecting the electrical activity of muscles associated with the blinking of the eyes of a user) that a user is currently blinking his/her eyes. Furthermore, the EEG and/or the EMG may be incorporated into a battery-powered mobile headset (e.g., styled as traditional headphones, hats/helmets, glasses, etc.) upon which the media guidance application is implemented and/or in communication with. The media guidance may initiate monitoring in response to a user input entered on the user device (e.g., turning the user device on), in response to detecting a change (or lack thereof) in brain activity, and/or based on a predetermined schedule (e.g., when a user typically wakes up from sleeping).

In some aspects, media guidance application (or a user device upon which the media guidance application is implemented) may manage power consumption of the user device based on brain activity of a user. For example, the media guidance application may operate in a plurality of modes each associated with a power consumption and/or sensitivity level. In response to the user request to monitor the brain activity of the user the media guidance application may initiate a first mode, and in response to detecting the brain activity of the user does not correspond to a threshold range of brain activity, the media guidance application may change from the first mode to the second mode and monitoring the brain activity of the user with the user device in the second mode.

For example, the media guidance application (or a user device upon which the media guidance application is implemented) may include a "sleep mode" (e.g., a lower powered/lower sensitivity mode) that is initiated after prolong periods of similar brain activity and/or repetitive brain activity cycles. For example, the media guidance application may initiate the sleep mode in response to determining that the brain activity of the user has dropped below a first threshold range (e.g., associated with an awake user). In another example, the media guidance application may detect that the brain activity of the user exceeds a second threshold range (e.g., associated with a sleeping user), and in response, initiate an "active mode."

In some aspects, a media guidance application may monitor the brain activity of a user and determine a first brain state of the user based on the brain activity. The first brain state (e.g., the current frequency range of voltage fluctuations in the brain and/or electrical activity of muscles near the brain at rest and during contraction) may correspond to a first mood of the user. The media guidance application may also select a second brain state (e.g., a preferred frequency range of voltage fluctuations in the brain and/or electrical activity of muscles near the brain at rest and during contraction) that corresponds to a second mood of the user. The media guidance application may compare the first brain state to the second brain state to determine whether the two states correspond (e.g., indicative of whether or not a user is currently in a preferred mood). In response to determining the first brain state does not correspond to the second brain state, the media guidance application may generate a display of a media asset to the user that is associated with inducing the second brain state.

For example, in response to determining that a user is not in a preferred mood, the media guidance application may generate for display one or more media assets associated with inducing a particular mood. Additionally or alternatively, in response to determining that the user is in a particular mood, the media guidance application may match media assets to that particular mood. To select a particular media asset, the media guidance application may compare the data associated with the current brain state of the user to a preferred, selected, and/or ideal brain state of the user.

To determine a mood corresponding to a brain state, the media guidance application may cross-reference data associated with the brain state of the user (e.g., the first frequency range and/or first electrical activity of the muscles near the brain) with a database associated with data related to brain states and corresponding moods. For example, based on the cross-reference, the media guidance application may determine that the data associated with the brain state of the user indicates that the user is happy, scared, etc. The media guidance may then select a second brain state (e.g., corresponding to a preferred mood, attentiveness level, etc.) based on a current time, a user input, a current activity, or a preferred biorhythmic pattern associated with the user.

To select a media asset, the media guidance application may cross-reference the second brain state with a database that includes a plurality of previous brain states of the user (e.g., representing various moods, attentiveness levels, etc.) and corresponding categories of media assets that the user was consuming during each of the previous brain states. In response to determining a media asset is of the category of media assets that the user was consuming during a previous brain state corresponding to the second brain state, the media guidance application generates a display of the media asset to the user.

In some aspects, the media guidance application may provide a user feedback associated with his/her brain activity. For example, the media guidance application may generate audio/visual cues related to a current brain state of the user and/or preferred brain state (or progress towards a preferred brain state) of the user. For example, the media guidance application may monitor the brain activity of the user associated with a first brain state that is associated with performing a first operation of the media guidance application (e.g., navigating about, or accessing a menu in, a media guide, selecting a media listing, performing a fast-access playback operation, etc.). The media guidance application may generate for display an icon on a display screen that provides feedback to the user related to achieving the first brain state, and in response to detecting a change in the brain activity of the user, adjust the icon on the display screen to reflect the change in the brain activity of the user.

The icon may include a graphical representation of the brain activity associated with a brain state of the user (e.g., a graph indicating a current attentiveness level associated with a user). and a graphical representation indicating the user's progress towards the first brain state (e.g., a graph indicting an attentiveness level goal and a user's current progress towards that goal). Additionally or alternatively, the icon may include textual information (e.g., descriptions of media guidance applications that may be performed and the brain states needed to trigger each operation) and/or instructions (e.g., instructions on how to achieve a particular brain state).

In some aspects, the media guidance application may perform one or more media guidance applications and/or brain activity operations in response to detecting particular brain activity and/or determining a user has achieved a particular brain state. For example, the media guidance application may detect an eye blink pattern of a user (and/or the brain activity indicative of an eye blink pattern). In response to detecting the eye blink pattern, the media guidance application may monitor brain activity associated with an attentiveness level of the user. The media guidance application may then cross-reference the brain activity associated with the attentiveness level of the user with a database associated with attentiveness levels and corresponding brain activity to determine the attentiveness level of the user. The media guidance application may then compare the attentiveness level of the user to a threshold attentiveness level, and in response to determining the attentiveness level of the user does not correspond to the threshold attentiveness level, the media guidance application may perform an operation associated with a low attentiveness level of the user.

For example, the media guidance application may in response to detecting one or more eye blinks of a user, initiate brain monitoring of the user. The media guidance application may then determine whether or not the user is paying attention (e.g., to a display device associated with the media guidance application). In response to determining (e.g., based on comparing the brain activity of the user to reference brain activity known to be associated with a particular level of attention (either of the user or of all users)) an attentiveness level of a user is below a threshold amount, the media guidance application performs an operation. The operation may be related to the attentiveness level of the user (e.g., generating a display of a different media asset, which may be of interest to the user).

Additionally, the media guidance application may continue to perform the same or different operation until it detects a change in the brain activity of the user (e.g., indicative of a subsequent eye blink pattern and/or a change in attentiveness level of the user). For example, in response to determining that the user is not paying attention or has lost interest in a current media asset (e.g., a song in a music playlist), the media guidance application may present a different media asset (e.g., skip to a different song in the music playlist).

In some aspects, the media guidance application may perform a media guidance application operation in response to activity detected in a particular region of the brain of a user. For example, the media guidance application may monitor brain activity of the user in a first region of the brain and determine a first brain state associated with the first region based on the monitored brain activity. The media guidance application may then cross-reference the first region with a database associated with functions performed by the user using regions of the brain to determine at least one function the user is performing based on the brain activity of the user in the first region of the brain. The media guidance application may then compare the first brain state to a threshold range for performing the at least one function, and in response to determining the first brain state does not correspond to the threshold range, performing a media guidance operation associated with the at least one function.

For example, the media guidance application may detect a state of the brain activity associated with the occipital lobe of the user. In response to determining that the occipital lobe is associated with the vision, the media guidance application may compare the current brain state of the user to typical brain states (e.g., of the user or all users) associated with viewing media assets (e.g., represented by a threshold range). In response to determining that the brain state of the user does not correspond to the typical brain state (e.g., indicating that the user is having difficulty seeing the media assets, the user is squinting, the media asset is too bright, etc.), the media guidance application may modify (e.g., increase the size of text on the display device, reduce a brightness setting of the display device, etc.) the media assets, display settings, etc. in order to align the brain state of the user with the typical brain state.

In another example, the media guidance application may detect a state of the brain activity associated with various regions of the brain in order to perform a function. For example, the media guidance application may detect a state of the brain activity associated with the occipital lobe (e.g., associated with vision) and the parietal lobe (e.g., associated with reading) of the user. In response to determining that the brain state of the brain activity associated with the occipital lobe (e.g., associated with vision) and the parietal lobe (e.g., associated with reading) of the user does not correspond to the typical brain state of a user, while the temporal lobe (e.g., associated with hearing) does correspond to the typical brain state of the user, the media guidance application may modify the media assets, display settings, etc. such that text or important events are communicated to the user via verbal means (e.g., audio announcements).

In some aspects, the media guidance application may perform media guidance application operations in response to changes in brain activity of a user. For example, the media guidance application may receive a user request to monitor the brain activity of the user with a user device and monitor the brain activity of the user. The media guidance application may then compare the brain activity of the user to a threshold range of brain activity, and in response to determining that the brain activity of the user does not correspond to the threshold range based on the comparison, instruct the user device to cease monitoring the brain activity of the user.

Additionally, in response to determining that the brain activity of the user does not correspond to the threshold range, the media guidance application may perform a media guidance application operation. For example, the media guidance application may record and/or pause a media asset currently being presented on a display device.

The media guidance application may also deactivate the user device in response to determining that the brain activity of the user does not correspond to the threshold range. For example, using an EEG and/or the EMG incorporated in to mobile headset, the media guidance application may determine that the brain activity of the user indicates that the user is currently awake. The media guidance application may monitor for a threshold range of brain activity (e.g., corresponding to a predetermined frequency range and amplitude) that indicates that the user has fallen asleep. In response to detecting that the user has fallen asleep, the media guidance application may power off the user device.

It should be noted, the systems, methods, apparatuses, and/or aspects described above may be applied to, or used in accordance with, other systems, methods, apparatuses, and/or aspects.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIG. 6 shows multiple user devices that may be associated with monitoring brain activity in accordance with some embodiments of the disclosure;

FIG. 9 is a flow-chart of illustrative steps involved in generating an icon associated with the brain activity of a user in accordance with some embodiments of the disclosure;

FIG. 14 is a flow-chart of illustrative steps involved in determining a function associated with particular brain activity in accordance with some embodiments of the disclosure;

FIG. 15 is a flow-chart of illustrative steps involved in changing a user device from one mode to another based on brain activity in accordance with some embodiments of the disclosure;

DETAILED DESCRIPTION OF DRAWINGS

Figure 1A:
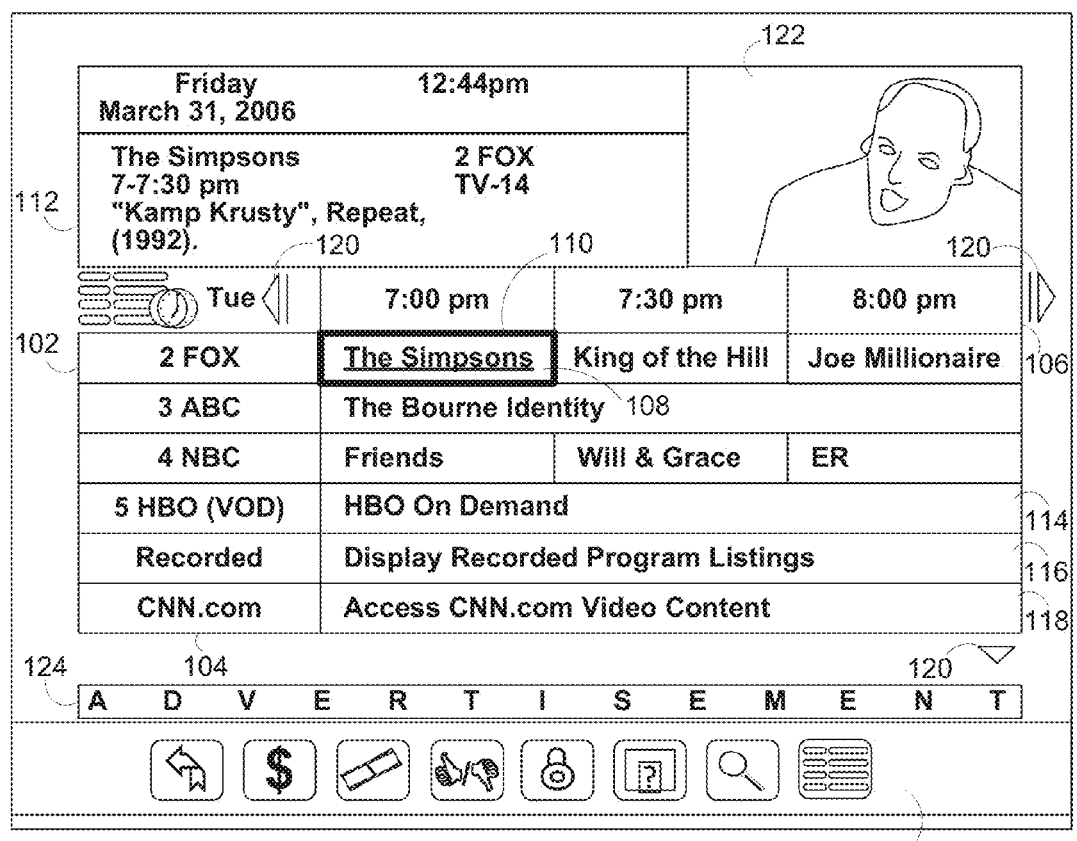
FIG. 1A shows an illustrative media guidance application for selecting media assets in accordance with some embodiments of the disclosure.

Method and systems are disclosed herein for a media guidance application configured to monitor brain activity. As the amount of content available to users in any given content delivery system can be substantial, many users desire a form of media guidance through an interface that allows users to efficiently navigate content selections and easily identify content that they may desire. An application that provides such guidance is referred to herein as an interactive media guidance application or, sometimes, a media guidance application or a guidance application.

Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content. As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, advertisements, chat sessions, social media, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

With the advent of the Internet, mobile computing, and high-speed wireless networks, users are accessing media on user equipment devices which they traditionally did not use. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same. In some embodiments, the user equipment device may have a front facing screen and a rear facing screen, multiple front screens, or multiple angled screens. In some embodiments, the user equipment device may have a front facing camera and/or a rear facing camera. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

In some embodiments, a user device may be configured to monitor brain activity upon which various media guidance application operations and features may be based. For example, based on brain activity information, the media guidance application may recommend media assets that correspond to a mood of a user or are likely to induce a preferred mood of the user, provide on-screen feedback about current brain activity of the user, adjust media assets and/or media guides in order to compensate for unusual brain activity in distinct areas of the brain, adjust power levels in the user device, and/or any combinations thereof.

In some embodiments, the user device may incorporate and/or have access to an electroencephalogram unit ("EEG"). An EEG measures electrical activity associated with a brain of a user. For example, an EEG may measure voltage fluctuations and/or the frequency or frequency range of voltage fluctuations generated by the brain of a user.

For example, an EEG may describe rhythmic brain activity. Rhythmic activity (e.g., activity associated with neural oscillation) also known as brain waves may be described in terms of frequency bands or frequency ranges. For example, a delta band includes a frequency range of up to about 4 Hz with a typical amplitude of 20-200 microvolts. Delta bands are, in some circumstances, associated with a sleeping state of a user. Theta bands include a frequency range of 4 to 8 Hz with a typical amplitude of 10 microvolts. Theta bands are, in some circumstances, associated with drowsiness. Alpha bands include a frequency range of 8 to 13 Hz with a typical amplitude of 20-200 microvolts. Alpha bands are, in some circumstances, associated with a relaxed state and/or the blinking of a user's eyes. Beta bands include frequencies of 13 to 30 Hz with a typical amplitude of 5-10 microvolts. Beta bands are, in some circumstances, associated with alertness, concentration, and/or anxiety. Gamma bands include a frequency range of 30 to 100 Hz and may have various amplitudes. Gamma bands are, in some circumstances, associated with combinations of senses of a user (e.g., sight, smell, sound, touch, taste) and/or short term memory. Frequency bands and frequency ranges as well as the symmetry of these bands and ranges across the brain of a user are also associated with various moods, which is discussed in detail in Rybak, "Frontal Alpha Power Asymmetry in Aggressive Children and Adolescents With Mood and Disruptive Behavior Disorders," Clinical EEL and Neuroscience, Vol. 3, 2006, which is hereby incorporated by reference herein in its entirety.

Additional discussion about the use of EEG's to detect a level of attention, engagement, frustration, anxiety, emotional state, and comprehension are discussed in detail in Wyczesany, Miroslaw et al., "Subjective mood estimation co-varies with spectral power EEG characteristics," Department of Psychophysiology, Jagiellonian University, Krakow, Poland, Acta Neurobiol Exp, 68: 180-192, 2008, Tan, Bao Hong, "Using a Low-cost EEG Sensor to Detect Mental States, CMU-CS-12-134, School of Computer Science, Carnegie Mellon University, August 2012, Hamadicharef et al., "Learning EEG-based Spectral-Spatial Patterns for Attention Level Measurement," Institute for Infocomm Research, 2009, Bos, Danny Oude, "EEG-based Emotion Recognition, The Influence of Visual and Auditory Stimuli," Department of Computer Science, University of Twente, 2006, and Pradeep et al., U.S. Pat. No. 8,392,250, issued Mar. 5, 2013, which are hereby incorporated by reference herein in their entirety.

In some embodiments, the user device incorporates and/or has access to an electromyogram unit ("EMG"). An EMG measures the electrical activity of muscles at rest and during contraction. The use of EMG and EEG for providing biofeedback is discussed in detail in Frank et al., "Biofeedback in medicine: who, when, why and how?" Ment. Health Fam. Med., June 2010, and Wartena et al., U.S. Patent Application Publication No. 2012/0029322, filed Mar. 24, 2010, which is hereby incorporated by reference herein in its entirety. In some embodiments, the user device may include additional components for detecting brain activity, moods, and attentiveness of a user as discussed in detail in Lee et al., U.S. Pat. No. 8,332,883, issued Dec. 11, 2012, and Bill, U.S. Pat. No. 8,373,768, issued Feb. 12, 2013, which are hereby incorporated by reference herein in their entirety.

In some embodiments, a user device may also distinguish between the different areas of the brain and the different functions of each area of the brain. For example, the frontal lobes are typically associated with planning, problem-solving, voluntary motor control, cognition, intelligence, attention, language processing and comprehension, and various emotions. The parietal lobe is typically associated with perception and integration of somatosensory information (e.g., touch, pressure, temperature, and pain) visuospatial processing, spatial attention, spatial mapping, and number representation. The occipital lobe is typically associated with vision, including color, orientation, and motion. The temporal lobe is typically associated with recognition, perception, hearing, smell, and memory. The regions and functions of the brain, in particular their effect on attention and emotion are discussed in detail in Yamasaki et al., "Dissociable prefrontal brain systems for attention and emotion," PNAS, vol. 99, no. 17, 2002, which is hereby incorporated by reference in its entirety.

In some embodiments, a user device may be configured as a headset. As used herein a "headset" refers to any device or article worn or affixed to a user for monitoring brain activity. For example, a user device for monitoring brain activity may be fashioned as a pair of headphones, a hat, a helmet, a pair of glasses, and/or other configuration for use by a user. In some embodiments, a headset may be powered by a local energy storage device (e.g., a battery). For example, in some embodiments, a headset may be rechargeable and/or include replaceable energy storage devices.

The media guidance application (or a user device upon which the media guidance application is implemented) may manage power consumption of the user device based on brain activity of a user. For example, the media guidance application may operate in a plurality of modes each associated with a power consumption and/or sensitivity level. For example, the media guidance application (or the user device upon which the media guidance application is implemented) may trigger various modes on the user device based on a change (or lack of change during a period of time) in brain activity (e.g., a brain state, frequency range, etc.).

Additionally or alternatively, the media guidance application (or the user device upon which the media guidance application is implemented) may trigger various modes on the user device for detecting brain activity based on the particular media guidance operation being performed (or not being performed). For example, the media guidance application may determine that a particular mode (e.g., with a particular power consumption level and/or sensitivity level) corresponds to determining a mood or a user, whereas a different mode corresponds to determining an attentiveness level of a user.

For example, in response to a user request to perform media guidance operations (e.g., schedule a recording) based on monitored brain activity, the media guidance application may initiate a first mode, and, in response to receiving a user request, to perform a different media guidance operation (e.g., recommend a media listing based on a mood of the user), the media guidance application may initiate a second mode. Furthermore, the media guidance application may automatically adjust the various modes initiated and/or switch from one mode to another. For example, in response to detecting the brain activity of the user does not correspond to a threshold range of brain activity (e.g., associated with actively performing media guidance application operations), the media guidance application may change from a first mode to the second mode (e.g., associated with non-actively performing media guidance applications). This "sleep" or "stand-by" mode may feature reduce power consumption levels and/or sensitivity levels, which may be beneficial in conserving energy consumption as well as reducing a user's exposure to the techniques used to monitor the brain activity.

For example, the media guidance application (or a user device upon which the media guidance application is implemented) may include a "sleep mode" (e.g., a lower powered/lower sensitivity mode) that is initiated after prolonged periods of similar brain activity and/or repetitive brain activity cycles (e.g., indicating that the user is sleeping, engaged in a repetitive activity, and/or does not currently need to perform any media guidance application operations. For example, the media guidance application may initiate the sleep mode in response to determining that the brain activity of the user has dropped below a first threshold range (e.g., associated with an awake user). In another example, the media guidance application may detect that the brain activity of the user exceeds a second threshold range (e.g., associated with a sleeping user), and in response, initiate an "active mode."

In some embodiments, a media guidance application (or a user device upon which the media guidance application is implemented) may detect and/or monitor brain activity of a user. In some embodiments, the media guidance application may determine whether or not the brain activity of a user corresponds to a threshold range. As referred to herein, a "threshold range" refers to a frequency range and/or amplitude of brain activity that defines the boundaries of a brain state. For example, a threshold range may be defined as a particular frequency range (in Hz) associated with a brain state of a user, may be defined as frequency bands associated with a brain state of a user, and/or may be defined according to any other measurement that describes the current, preferred, past, and/or future brain state of a user. In some embodiments, a threshold range may account for any transient variations and amplitudes in brain state. For example, a threshold range may be defined as an average amplitude, frequency, frequency range, and/or frequency band over a particular period of time. In addition, a threshold range may refer to a composite range that includes one or more amplitudes and/or frequencies associated with one or more waves. For example, in some embodiments, a particular brain state may correspond to brain activity corresponding to theta bands with a first amplitude and delta bands at a second amplitude.

It should also be noted that in some embodiments, a threshold range may itself include one or more threshold ranges. For example, a threshold range associated with one brain state (e.g., a user being awake) may itself include numerous other threshold ranges (e.g., a mood of the user, an attentiveness level of the user, etc.).

As referred to herein, a "brain state" refers to a qualitative assessment of the mood, level of anxiety, level of attentiveness, level of comprehension, level of proficiency associated with one or more functions (e.g., reading text on a screen, hearing audio, etc.) of a user, and/or a combination thereof associated with the brain activity of the user. A brain state can be quantified as corresponding to a particular threshold range, and different brain states may be compared based on their corresponding threshold ranges.

Brain states may be identified by a user device (e.g., upon which a media guidance application is implemented) that incorporates and/or have access to a device for monitoring brain waves (e.g., an EEG, EMG, and/or any other device discussed herein). The media guidance application may monitor the brain activity (e.g., brain waves) of a user and determine a first brain state of the user based on the brain activity. The first brain state (e.g., the current frequency range of voltage fluctuations in the brain, electrical activity of muscles near the brain at rest and during contraction, and/or threshold range) may correspond to a first mood of the user. The media guidance application may also select a second brain state (e.g., a preferred frequency range of voltage fluctuations in the brain, electrical activity of muscles near the brain at rest and during contraction, and/or threshold range) that corresponds to a second mood of the user. The media guidance application may compare the first brain state to the second brain state (e.g., compare the frequency range of voltage fluctuations in the brain, electrical activity of muscles near the brain at rest and during contraction, and/or threshold range associated with the first state to the frequency range of voltage fluctuations in the brain, electrical activity of muscles near the brain at rest and during contraction, and/or threshold range associated with the second state) to determine whether two states corresponds (e.g., indicate the same frequency range of voltage fluctuations in the brain, electrical activity of muscles near the brain at rest and during contraction, and/or threshold range). In response to determining the first brain state does not corresponds to the second brain state, the media guidance application may generate a display of a media asset to the user that is associated with inducing the second brain state.

For example, in response to determining that a user is not in a preferred mood, the media guidance application may generate for display one or more media assets associated with inducing a particular mood. Additionally or alternatively, in response to determining that the user is in a particular mood, the media guidance application may match media assets to that particular mood. To select a particular media asset, the media guidance application may compare the data associated with the current brain state of the user to a preferred, selected, and/or ideal brain state of the user.

To determine a mood corresponding to a brain state, the media guidance application may cross-reference data associated with the brain state of the user (e.g., a frequency range, an electrical activity of the muscles near the brain, and/or a threshold range) with a database associated with data related to brain states and corresponding moods. For example, based on the cross-reference, the media guidance application may determine that the data associated with the brain state of the user indicates that the user is confused, nervous, etc. The media guidance may then select a new brain state (e.g., corresponding to a preferred mood, attentiveness level, etc.) based on a current time, a user input, a current activity, or a preferred biorhythmic pattern associated with the user.

For example, the media guidance application may receive instructions from the user indicating that the user wishes to be in a particular mood (e.g., happy) every evening at six o'clock PM. In response, the media guidance application may ensure the user is happy at that time by generating a display of a media asset that is associated with happiness of the user at six o'clock PM. In another example, the media guidance application may receive instructions from the user indicating that the user wishes to follow a particular schedule for his/her biorhythmic activity (e.g., the user wishes to maintain a therapeutic gradual increase and decrease in brain activity, frequency bands, etc.) In response, the media guidance ensures the brain activity of the user corresponds to the schedule, and if not, generates a display of a media asset (e.g., a movie that corresponds to the current brain activity of the schedule, a display of textual instructions such as "Calm Down," "Relax," "Breath Deeply," "Concentrate," associated with maintaining the schedule).

To select a media asset for display, the media guidance application may cross-reference a preferred brain state with a database that includes a plurality of previous brain states of the user (e.g., representing various moods, attentiveness levels, etc.) and corresponding categories of media assets that the user was consuming during each of the previous brain states. In response to determining a media asset is of the category of media assets that the user was consuming during a previous brain state corresponding to the second brain state, the media guidance application selects the media asset for display to the user.

The media guidance application may also calibrate and/or perform a training/set-up mode. For example, the media guidance application may receive information from the user, in which the user describes and/or rates current brain states of the user. For example, during calibration, the media guidance application may detect a brain state and ask the user to describe the brain (e.g., designate the state as associated with a particular mood). The current brain state of the user (e.g., the current threshold range) will then be designated as corresponding to the particular mood. Additionally or alternatively, the media guidance application may receive instructions designating a particular brain state as corresponding to a particular mood. For example, the media guidance application may retrieve/receive instructions that indicate that a threshold range of 8 to 10 Hz indicates that the particular user is in a happy mood. Additionally, the media guidance application may retrieve/receive instructions that indicate that a threshold range of 10 to 13 Hz indicates that the particular user is in a sad mood. In another example, if the average amplitude of a threshold range is 50 microvolts and an average frequency range is 7 Hz, the media guidance application may determine that the threshold range indicates that a user is currently anxious.

The media guidance application may also offer training opportunities. For example, the media guidance application may generate for display media assets in sequence in order to sway or induce a user into a particular brain state. The media guidance application may also offer tips or instructions for achieving a particular brain state. For example, the media guidance application may generate on-screen instructions for achieving and/or maintaining particular brain states (e.g., moods, attentiveness levels, etc.).

The media guidance application may perform numerous operations for the user. As referred to herein, a "media guidance application operation" refers to any operation corresponding to providing, receiving, and generating media guidance data for consumption by a user. For example, media guidance application operations include displaying media guidance data, providing options to navigate, select, and edit media guidance data or content (e.g., a media asset) associated with media guidance data, and/or manipulating a device used to access (e.g., a display device), retrieve (e.g., a server), and/or associate media guidance data with a user (e.g., a user device for monitoring brain activity). One of the operations of the media guidance application is to provide media guidance data to users. As referred to herein, the phrase, "media guidance data" or "guidance data" should be understood to mean any data related to content, such as media listings, media-related information (e.g., broadcast times, broadcast channels, titles, descriptions, ratings information (e.g., parental control ratings, critic's ratings, etc.), genre or category information, actor information, logo data for broadcasters' or providers' logos, etc.), media format (e.g., standard definition, high definition, 3D, etc.), advertisement information (e.g., text, images, media clips, etc.), on-demand information, blogs, websites, and any other type of guidance data that is helpful for a user to navigate among and locate desired content selections.

Other operations of a media guidance application are to play media assets and provide fast access playback operations for those media assets. As referred to herein, the phrase "fast-access playback operations" should be understood to mean any operation that pertains to playing back a non-linear media asset faster than normal playback speed or in a different order than the media asset is designed to be played, such as a fast-forward, rewind, skip, chapter selection, segment selection, skip segment, jump segment, next segment, previous segment, skip advertisement or commercial, next chapter, previous chapter or any other operation that does not play back the media asset at normal playback speed. The fast-access playback operation may be any playback operation that is not "play," where the play operation plays back the media asset at normal playback speed.

FIGS. 1A-C and 2 show illustrative display screens that may be used to provide media guidance data. The display screens shown in FIGS. 1A-C and 2 may be implemented on any suitable user equipment device or platform. While the displays of FIGS. 1A-C and 2 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria. The organization of the media guidance data is determined by guidance application data. As referred to herein, the phrase, "guidance application data" should be understood to mean data used in operating the guidance application, such as program information, guidance application settings, user preferences, or user profile information.

FIG. 1A shows illustrative grid program listings display 100 arranged by time and channel that also enables access to different types of content in a single display. Display 100 may include grid 102 with: (1) a column of channel/content type identifiers 104, where each channel/content type identifier (which is a cell in the column) identifies a different channel or content type available; and (2) a row of time identifiers 106, where each time identifier (which is a cell in the row) identifies a time block of programming. Grid 102 also includes cells of program listings, such as program listing 108, where each listing provides the title of the program provided on the listing's associated channel and time. With a user input device, a user can select program listings by moving highlight region 110. Information relating to the program listing selected by highlight region 110 may be provided in program information region 112. Region 112 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L. P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g. FTP).

Grid 102 may provide media guidance data for non-linear programming including on-demand listing 114, recorded content listing 116, and Internet content listing 118. A display combining media guidance data for content from different types of content sources is sometimes referred to as a "mixed-media" display. Various permutations of the types of media guidance data that may be displayed that are different than display 100 may be based on user selection or guidance application definition (e.g., a display of only recorded and broadcast listings, only on-demand and broadcast listings, etc.). As illustrated, listings 114, 116, and 118 are shown as spanning the entire time block displayed in grid 102 to indicate that selection of these listings may provide access to a display dedicated to on-demand listings, recorded listings, or Internet listings, respectively. In some embodiments, listings for these content types may be included directly in grid 102. Additional media guidance data may be displayed in response to the user selecting one of the navigational icons 120. (Pressing an arrow key on a user input device may affect the display in a similar manner as selecting navigational icons 120.)

Display 100 may also include video region 122, advertisement 124, and options region 126. Video region 122 may allow the user to view and/or preview programs that are currently available, will be available, or were available to the user. The content of video region 122 may correspond to, or be independent from, one of the listings displayed in grid 102. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Advertisement 124 may provide an advertisement for content that, depending on a viewer's access rights (e.g., for subscription programming), is currently available for viewing, will be available for viewing in the future, or may never become available for viewing, and may correspond to or be unrelated to one or more of the content listings in grid 102. Advertisement 124 may also be for products or services related or unrelated to the content displayed in grid 102. Advertisement 124 may be selectable and provide further information about content, provide information about a product or a service, enable purchasing of content, a product, or a service, provide content relating to the advertisement, etc. Advertisement 124 may be targeted based on a user's profile/preferences, monitored user activity, the type of display provided, or on other suitable targeted advertisement bases.

While advertisement 124 is shown as rectangular or banner shaped, advertisements may be provided in any suitable size, shape, and location in a guidance application display. For example, advertisement 124 may be provided as a rectangular shape that is horizontally adjacent to grid 102. This is sometimes referred to as a panel advertisement. In addition, advertisements may be overlaid over content or a guidance application display or embedded within a display. Advertisements may also include text, images, rotating images, video clips, or other types of content described above. Advertisements may be stored in a user equipment device having a guidance application, in a database connected to the user equipment, in a remote location (including streaming media servers), or on other storage means, or a combination of these locations. Providing advertisements in a media guidance application is discussed in greater detail in, for example, Knudson et al., U.S. Patent Application Publication No. 2003/0110499, filed Jan. 17, 2003; Ward, III et al. U.S. Pat. No. 6,756,997, issued Jun. 29, 2004; and Schein et al. U.S. Pat. No. 6,388,714, issued May 14, 2002, which are hereby incorporated by reference herein in their entireties. It will be appreciated that advertisements may be included in other media guidance application display screens of the embodiments described herein.

Options region 126 may allow the user to access different types of content, media guidance application displays, and/or media guidance application features. Options region 126 may be part of display 100 (and other display screens described herein), or may be invoked by a user by selecting an on-screen option or pressing a dedicated or assignable button on a user input device. The selectable options within options region 126 may concern features related to program listings in grid 102 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.allrovi.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 4. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

Figure 1B:
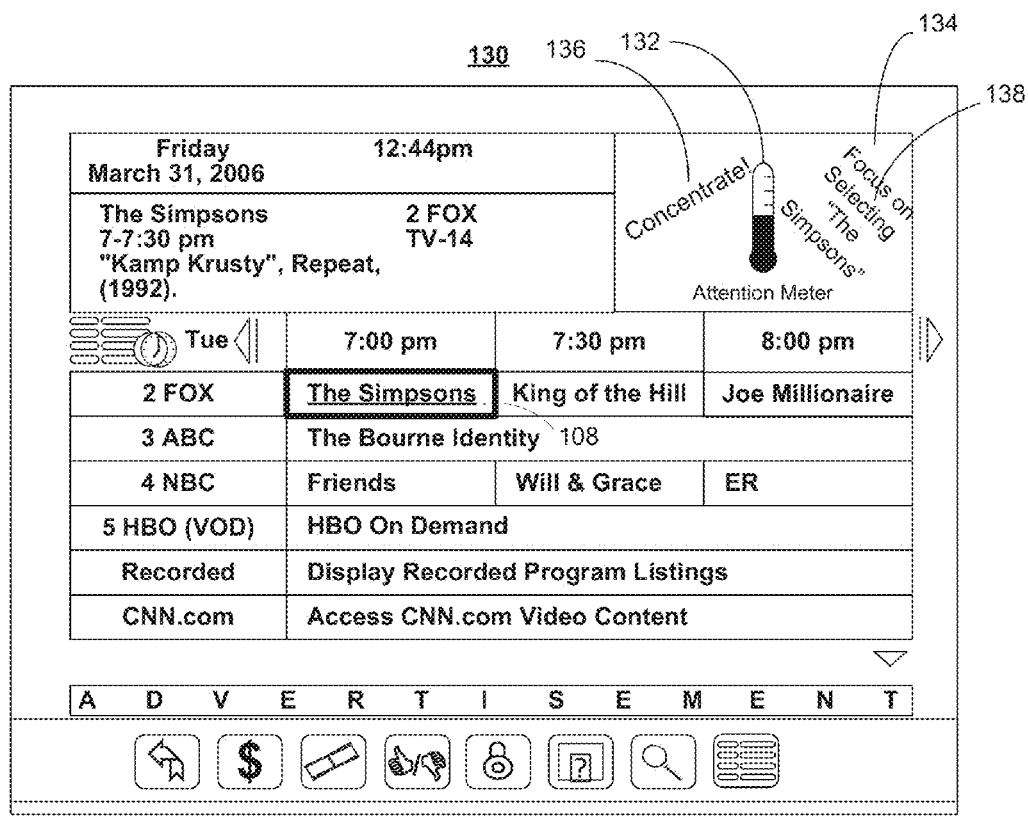
FIG. 1B shows an illustrative media guidance application for selecting media assets featuring an on-screen icon associated with brain activity of a user in accordance with some embodiments of the disclosure.

FIG. 1B shows an illustrative media guidance application for selecting media assets featuring an on-screen icon associated with brain activity of a user. For example, in some embodiments, the media guidance application may generate a display of an on-screen icon that provides feedback to a user regarding the user's current brain activity.

For example, in order to provide a user with guidance related to performing media guidance application operations using their brain waves, the media guidance application may provide a user feedback associated with his/her brain activity. For example, the media guidance application may generate audio/visual cues related to a current brain state of the user and/or preferred brain state (or progress towards a preferred brain state) of the user. For example, the media guidance application may monitor the brain activity of the user associated with a first brain state that is associated with performing a first operation of the media guidance application (e.g., navigating about, or accessing a menu in, a media guide, selecting a media listing, performing a fast-access playback operation, etc.). The media guidance application may generate for display an icon on a display screen that provides feedback to the user related to achieving the first brain state, and in response to detecting a change in the brain activity of the user, the media guidance application may adjust the icon on the display screen to reflect the change in the brain activity of the user.

The icon may include a graphical representation of the brain activity associated with a brain state of the user (e.g., a graph indicating a current attentiveness level associated with a user). and a graphical representation indicating the user's progress towards the first brain state (e.g., a graph indicting an attentiveness level goal and a user's current progress towards that goal). Additionally or alternatively, the icon may include textual information (e.g., descriptions of media guidance applications that may be performed and the brain states needed to trigger each operation) and/or instructions (e.g., instructions on how to achieve a particular brain state). Additionally or alternatively, the icon may include audio information (e.g., sound effects, verbal instructions, etc.).

In FIG. 1B, the media guidance application has currently generated a display of icon 134 on display 130. Icon 134 has several graphical representations. For example, icon 134 includes graphical representation 132 of an "Attention Meter," which indicates a current attentiveness level of the user. The "Attention Meter" appears as a thermometer, which when full (e.g., representing a particular threshold level of attentiveness) may trigger a particular media guidance application operation.

As used herein, a "threshold attentiveness level" refers to a particular attentiveness level required for the media guidance application to perform an operation. For example, in response to detecting that the current attentiveness level of a user exceeds the threshold attentiveness level, the media guidance application may perform a particular media guidance application operation (e.g., generated a display of a currently highlighted program).

The use of a graphical and/or animated representation in icon 134 provides an intuitive system through which to provide feedback to a user regarding the brain activity of the user. Additionally or alternatively, the media guidance application may generate other graphical representation in the form of any element that conveys a particular message to a user (e.g., whether a graph, video clip, inspiration message, etc.).

Icon 134 also includes several graphical representations that are textual elements. The graphical representations may serve multiple purposes. For example, while an animated meter may provide a user with his/her current progress related to performing one or more media guidance application operations, textual elements may provide a user instructions for performing a media guidance application operations (e.g., what brain state is needed to trigger the media guidance application operation) and/or indications of what media guidance application operations are available. For example, icon 134 includes a textual element 136 of "Concentrate!" that indicates to a user that the user needs to concentrate (e.g., increase his/her attentiveness level) to perform a particular media guidance application operation.

In addition, icon 134 includes textual element 138, which indicates to the user a particular media guidance application operation that is available. Textual element 138 states, "Focus on Selecting 'The Simpsons'". For example, the media guidance application may respond to detecting a threshold attentiveness level of the user by selecting a currently highlighted object (e.g., program listing 108); therefore, the media guidance application may provide textual element 138 to inform the user of the result of his/her attentiveness level.

In some embodiments, icon 134 may also indicate media guidance application operations that may occur in response to not detecting a particular brain state. For example, if the user does not achieve a brain state corresponding to a level of attentiveness that exceeds a threshold attentiveness level, the media guidance application may automatically perform a particular media guidance application operation.

Figure 1C:
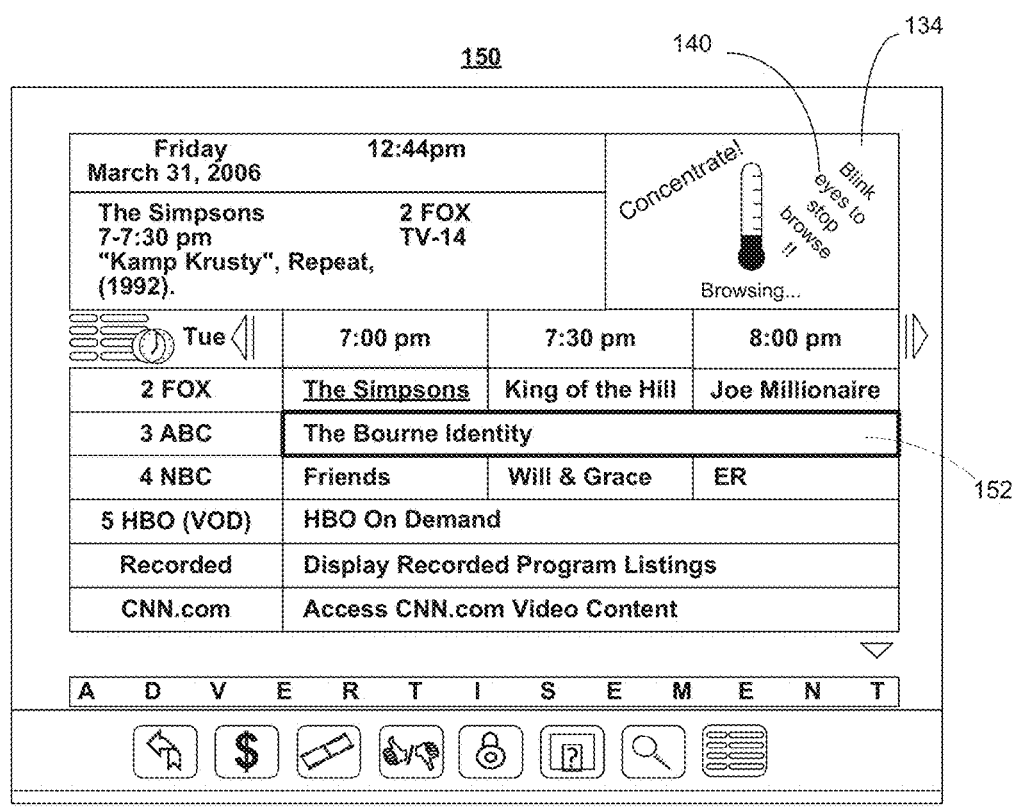
FIG. 1C shows an illustrative media guidance application for selecting media assets featuring an on-screen icon indicating a user currently has a low attentiveness level in accordance with some embodiments of the disclosure.

For example, FIG. 1C shows an illustrative media guidance application for selecting media assets featuring an on-screen icon indicating a user currently has a low attentiveness level. In FIG. 1C, a user did not achieve a threshold attentiveness level (e.g., in a particular time period), and in response, the media guidance application has automatically, without user input, performed a browse operation (e.g., the browse operation may include scrolling from one program listing to another program listing in a media guide, scrolling from one time/date to a different time/date, etc.). As shown in display 150, the media guidance application has initiated a browse operation and program listing 152 is now highlighted.

In display 150, icon 134 now includes new graphical representations that correspond to the media guidance application operation currently being performed. For example, the media guidance applications has now generated a display of icon 134 which includes textual element 140 that instructs a user to "Blink eyes to stop browsing!!" Consequently, in some embodiments, in response to detecting brain activity associated with a user blinking his/her eyes, the media guidance application may halt the browse operation (e.g., the media guidance application may stop scrolling through media listings and remain on a single media listing).

Figure 2:
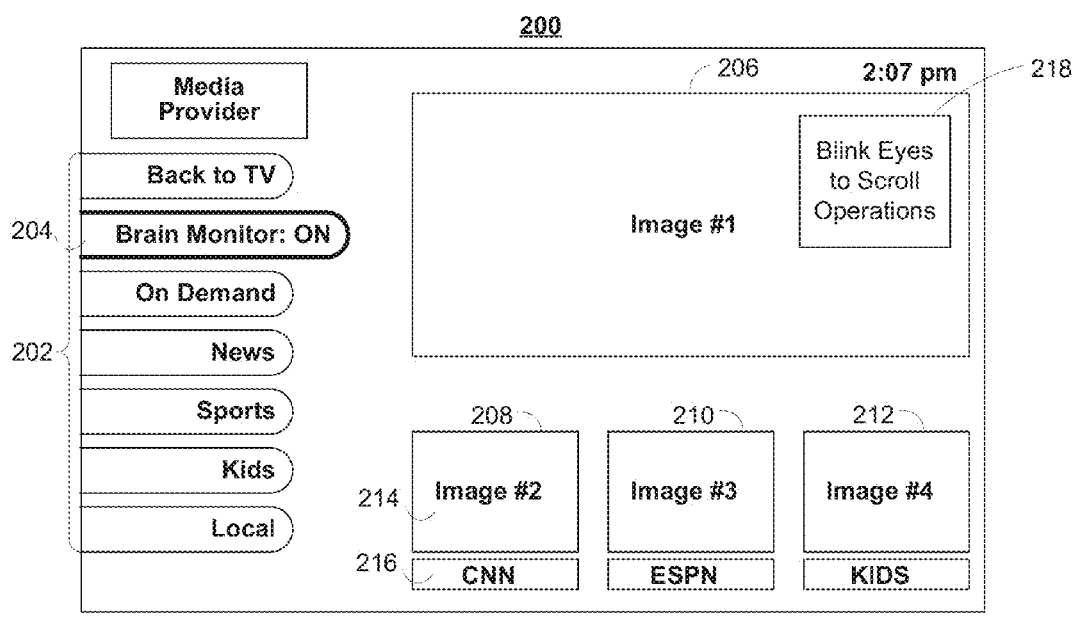
FIG. 2 shows an illustrative media guidance application that may be used to adjust user settings in accordance with some embodiments of the disclosure.

Another display arrangement for providing media guidance is shown in FIG. 2. Video mosaic display 200 includes selectable options 202 for content information organized based on content type, genre, and/or other organization criteria. In display 200, selectable option 204 is selected, thus initiating brain monitoring of a user. In some embodiments, selecting selectable option 204 may switch a user device configured to monitor the brain activity of a user from a first mode (e.g., a "sleep mode") to a second mode (e.g., an "active mode").

In response to selectable option 204 being selected, the media guidance application has also generated a display of icon 218, which instructs a user regarding the monitoring of brain activity. For example, icon 218 instructs a user to blink his/her eyes in order to scroll the different media guidance application operations that are available. For example, the media guidance application may scroll all available media guidance application operations, select a particular operation to monitor for, etc. based on receiving a corresponding eye blink pattern from a user.

As used herein, an "eye blink pattern" refers to a combination of blinks of a user and pauses before or after a blink that causes the media guidance application to perform an action. For example, the media guidance application may be configured to respond to particular eye blink patterns, which may be detected while monitoring brain activity. For example, the media guidance application may monitor alpha bands (e.g., typically associated with eye blinking) in the globus pallidus of the basal ganglia (e.g., the area of the brain typically associated with controlling eye blinking) of a user in order to detect an eye blink pattern. It should be noted that in some embodiments, an eye blink pattern may include only a single blink.

In display 200 listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listings 208, 210, and 212 may include more than one portion, including media portion 214 and text portion 216. Media portion 214 and/or text portion 216 may be selectable to view content in full-screen or to view information related to the content displayed in media portion 214 (e.g., to view listings for the channel that the video is displayed on).

The listings in display 200 are of different sizes (i.e., listing 206 is larger than listings 208, 210, and 212), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Dec. 29, 2005, which is hereby incorporated by reference herein in its entirety.

Figure 3:
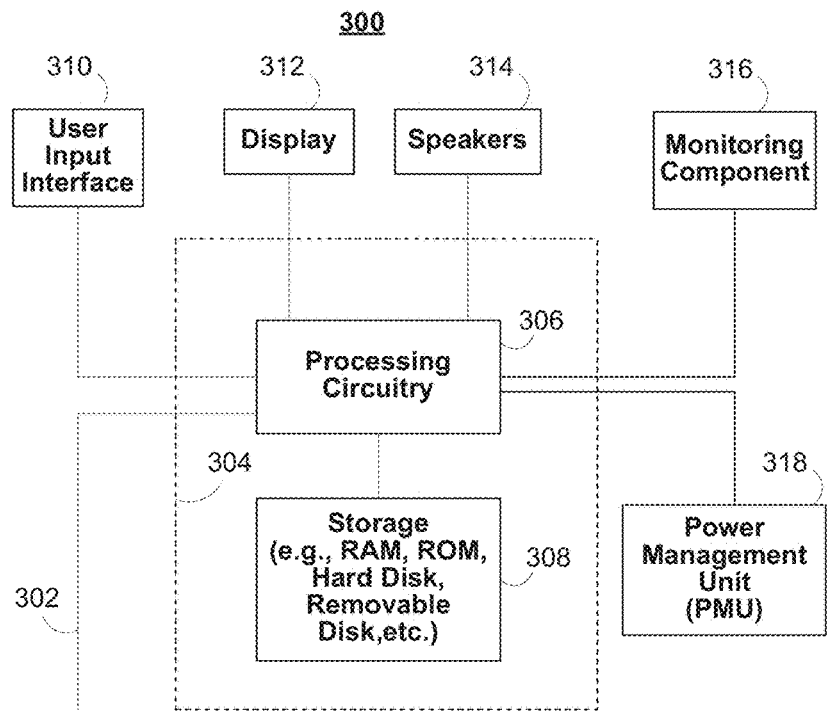
FIG. 3 is a block diagram of an illustrative user equipment device in accordance with some embodiments of the disclosure.

Users may access content and the media guidance application (and its display screens described above and below) from one or more of their user equipment devices. FIG. 3 shows a generalized embodiment of illustrative user equipment device 300. More specific implementations of user equipment devices are discussed below in connection with FIG. 4. User equipment device 300 may receive content and data via input/output (hereinafter "I/O") path 302. I/O path 302 may provide content (e.g., broadcast programming, on-demand programming, Internet content, content available over a local area network (LAN) or wide area network (WAN), and/or other content) and data to control circuitry 304, which includes processing circuitry 306 and storage 308. Control circuitry 304 may be used to send and receive commands, requests, and other suitable data using I/O path 302. I/O path 302 may connect control circuitry 304 (and specifically processing circuitry 306) to one or more communications paths (described below). I/O functions may be provided by one or more of these communications paths, but are shown as a single path in FIG. 3 to avoid overcomplicating the drawing.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for a media guidance application stored in memory (i.e., storage 308). Specifically, control circuitry 304 may be instructed by the media guidance application to perform the functions discussed above and below. For example, the media guidance application may provide instructions to control circuitry 304 to generate the media guidance displays. In some implementations, any action performed by control circuitry 304 may be based on instructions received from the media guidance application.

In client-server based embodiments, control circuitry 304 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 4). In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 308 may be used to store various types of content described herein as well as media guidance information, described above, and guidance application data, described above. Nonvolatile memory may also be used (e.g., to launch a boot-up routine and other instructions). Cloud-based storage, described in relation to FIG. 4, may be used to supplement storage 308 or instead of storage 308.

Control circuitry 304 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of the user equipment 300. Circuitry 304 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 308 is provided as a separate device from user equipment 300, the tuning and encoding circuitry (including multiple tuners) may be associated with storage 308.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. Display 312 may be provided as a stand-alone device or integrated with other elements of user equipment device 300. Display 312 may be one or more of a monitor, a television, a liquid crystal display (LCD) for a mobile device, or any other suitable equipment for displaying visual images. In some embodiments, display 312 may be HDTV-capable. In some embodiments, display 312 may be a 3D display, and the interactive media guidance application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304. Speakers 314 may be provided as integrated with other elements of user equipment device 300 or may be stand-alone units. The audio component of videos and other content displayed on display 312 may be played through speakers 314. In some embodiments, the audio may be distributed to a receiver (not shown), which processes and outputs the audio via speakers 314.

Control circuitry 304 may also instruct monitoring component 316. Monitoring component 316 may include one or more additional sub-components (e.g., an EEG, EMG, etc.) for monitoring brain activity of a user. Monitoring component 316 may transmit updates (e.g., associated with brain activity) of a user to control circuitry 304. Control circuitry 304 may compare the updates to data related to brain activity (e.g., threshold ranges, frequency ranges, etc.) of the user and/or other users stored on storage 308 (e.g., to determine whether or not the brain activity of the user corresponds to a particular threshold range and/or mood, attentiveness level, etc.).

It should be noted, monitoring component 316 may, in some embodiments, be located on a separate device in communication with the device upon which a media guidance application (and control circuitry 304) is implemented. For example, in some embodiments, monitoring component 316 may communication with device 300 via a communications network (e.g., communications network 414 (FIG. 4)).

Control circuitry 304 may also instruct power management unit (PMU) 318 to switch user equipment device 300 from a first power mode of operation to a second power mode of operation. Alternatively, PMU 318 may receive instructions to perform the switching directly over communications network 414. For example, monitoring component 316 may send PMU 318 a message telling it to switch user equipment device 300 from a first power mode to a second power mode.

As referred to herein, a first power mode may be a low power mode of operation. A first power mode may be understood to be a sleep mode, a standby mode, a power-off mode, a dormant mode, or a low-power mode. A low-power mode may refer to a mode of operation wherein user equipment device 300 has sufficient power to perform basic computation (e.g., compute whether an update should be performed) using processing circuitry 306 but insufficient power to perform more power-intensive tasks such as communicate with remote devices (e.g., media content source 416 (FIG. 4)) over communications network 414 (FIG. 4) and/or have limited capability to identify brain activity. As referred to herein, a second power mode may be a high power mode of operation. A second power mode may be understood to be an awake mode, an active mode, a full-power mode, a high-power mode, or an update mode, where a device operating at a second power mode has sufficient power to provide updates on brain activity of a user sufficient for determining a mood, attentiveness level, etc. A device operating at a second power mode may consume more power than when operating at a first power mode. In some embodiments, device 300 may operate at a third power mode, wherein the power consumed at the third power mode is greater than that consumed at the first power mode but less than that consumed at the second power mode. A third power mode may be an update mode, wherein device 300 operates at enough power to perform updates but not at full-power mode to perform media guidance application operations. A third power mode may also refer to a low-power mode, as described above. All three modes of operation (e.g., first power mode, second power mode, third power mode) may be used interchangeably within the present disclosure.

Once user equipment device 300 is switched to a second power mode of operation, control circuitry 304 updates the media guidance application with data from monitoring component 316 and stores the data in storage 308. As referred to herein, switching refers to activating a component of circuitry within user equipment device 300 that corresponds to a desired power mode of operation. Switching may be performed by PMU 318 to switch user equipment device 300 from a first power mode to a second power mode. A first power mode may correspond to a first circuitry component, and a second power mode may correspond to a second circuitry component. As referred to herein, switching from a first power mode to a second power mode involves deactivating the first circuitry component and activating a second circuitry component.

PMU 318 monitors and manages the power consumption of user equipment device 300. PMU 318 may be configured to monitor the current level of power consumption of user equipment device 300 based on device characteristics such as, but are not limited to, battery usage information, screen brightness, screen saver settings, central processing unit (CPU) power usage, graphic processing unit (GPU) power usage, integrated processor power usage, number of applications currently running on user equipment device 300, number and frequency of recordings scheduled to be performed on user equipment device 300, and the current power mode of operation (e.g., first power mode, second power mode) in addition to brain activity. More specifically, PMU 318 monitors the power state of user equipment device 300 to determine when device 300 switches from a first power mode to a second power mode. In some embodiments, PMU 318 may reside on user equipment device 300 as a component of control circuitry 304. In other embodiments, PMU 318 may be a unit that is external to user equipment device 300. In these cases, PMU 318 may communicate with user equipment device 300 by sending and receiving instructions from control circuitry 304.

PMU 318 may perform the switching in response to various conditions, based on instructions from control circuitry 304. In some embodiments, control circuitry 304 may receive an indication to switch user equipment device 300 from a first power mode to a second power mode. For example, control circuitry 304 may receive a request from a user input interface 310 or monitoring component 316 to perform the switching. In another example, control circuitry 304 may receive over communications network 414 (FIG. 4) via path 302 a message from a remote server indicating that user equipment device 300 should be switched to a second power mode of operation. In each of the aforementioned examples, control circuitry 304 may instruct PMU 318 to switch user equipment device 300 to a second power mode of operation in response to the requests and messages received. These messages and/or requests may include a time field which indicates a future time at which control circuitry 304 should switch device 300 to a second power mode to receive updates over network 414 (FIG. 4) and/or perform updates that are stored in storage 308. This time field may set a timer to switch user device 300 to a second power mode at a specified time. The time field may also set a timer to switch user device 300 to a first power mode at a specified time period when no updates will be sent to device 300.

The guidance application may be implemented using any suitable architecture. For example, it may be a stand-alone application wholly implemented on user equipment device 300. In such an approach, instructions of the application are stored locally, and data for use by the application is downloaded on a periodic basis (e.g., from an out-of-band feed, from an Internet resource, or using another suitable approach). In some embodiments, the media guidance application is a client-server based application. Data for use by a thick or thin client implemented on user equipment device 300 is retrieved on-demand by issuing requests to a server remote to the user equipment device 300. In one example of a client-server based guidance application, control circuitry 304 runs a web browser that interprets web pages provided by a remote server.

In some embodiments, the media guidance application is downloaded and interpreted or otherwise run by an interpreter or virtual machine (run by control circuitry 304). In some embodiments, the guidance application may be encoded in the ETV Binary Interchange Format (EBIF), received by control circuitry 304 as part of a suitable feed, and interpreted by a user agent running on control circuitry 304. For example, the guidance application may be an EBIF application. In some embodiments, the guidance application may be defined by a series of JAVA-based files that are received and run by a local virtual machine or other suitable middleware executed by control circuitry 304. In some of such embodiments (e.g., those employing MPEG-2 or other digital media encoding schemes), the guidance application may be, for example, encoded and transmitted in an MPEG-2 object carousel with the MPEG audio and video packets of a program.

Figure 4:
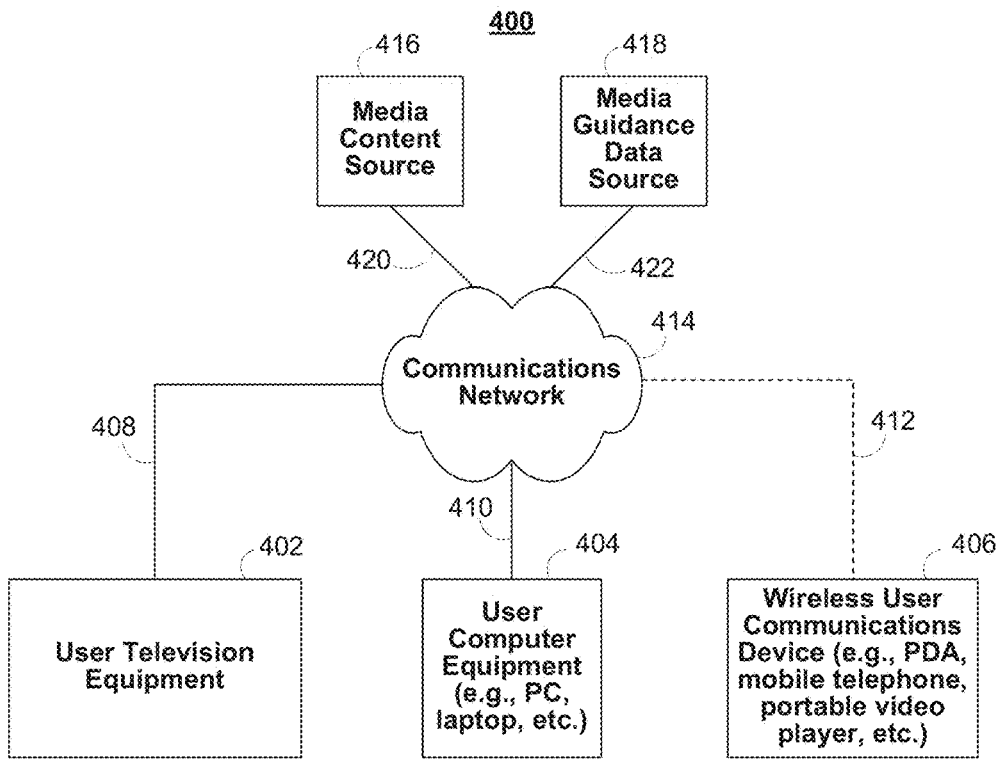
FIG. 4 is a block diagram of an illustrative media system in accordance with some embodiments of the disclosure.

User equipment device 300 of FIG. 3 can be implemented in system 400 of FIG. 4 as user television equipment 402, user computer equipment 404, wireless user communications device 406, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 3 may not be classified solely as user television equipment 402, user computer equipment 404, or a wireless user communications device 406. For example, user television equipment 402 may, like some user computer equipment 404, be Internet-enabled allowing for access to Internet content, while user computer equipment 404 may, like some television equipment 402, include a tuner allowing for access to television programming. The media guidance application may have the same layout on various different types of user equipment or may be tailored to the display capabilities of the user equipment. For example, on user computer equipment 404, the guidance application may be provided as a web site accessed by a web browser. In another example, the guidance application may be scaled down for wireless user communications devices 406.

In system 400, there is typically more than one of each type of user equipment device but only one of each is shown in FIG. 4 to avoid overcomplicating the drawing. In addition, each user may utilize more than one type of user equipment device and also more than one of each type of user equipment device.

In some embodiments, a user equipment device (e.g., user television equipment 402, user computer equipment 404, wireless user communications device 406) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.allrovi.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 414. Namely, user television equipment 402, user computer equipment 404, and wireless user communications device 406 are coupled to communications network 414 via communications paths 408, 410, and 412, respectively. Communications network 414 may be one or more networks including the Internet, a mobile phone network, mobile voice or data network (e.g., a 4G or LTE network), cable network, public switched telephone network, or other types of communications network or combinations of communications networks. Paths 408, 410, and 412 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 412 is drawn with dotted lines to indicate that in the exemplary embodiment shown in FIG. 4 it is a wireless path and paths 408 and 410 are drawn as solid lines to indicate they are wired paths (although these paths may be wireless paths, if desired). Communications with the user equipment devices may be provided by one or more of these communications paths, but are shown as a single path in FIG. 4 to avoid overcomplicating the drawing.

Although communications paths are not drawn between user equipment devices, these devices may communicate directly with each other via communication paths, such as those described above in connection with paths 408, 410, and 412, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 414.

System 400 includes content source 416 and media guidance data source 418 coupled to communications network 414 via communication paths 420 and 422, respectively. Paths 420 and 422 may include any of the communication paths described above in connection with paths 408, 410, and 412. Communications with the content source 416 and media guidance data source 418 may be exchanged over one or more communications paths, but are shown as a single path in FIG. 4 to avoid overcomplicating the drawing. In addition, there may be more than one of each of content source 416 and media guidance data source 418, but only one of each is shown in FIG. 4 to avoid overcomplicating the drawing. (The different types of each of these sources are discussed below.) If desired, content source 416 and media guidance data source 418 may be integrated as one source device. Although communications between sources 416 and 418 with user equipment devices 402, 404, and 406 are shown as through communications network 414, in some embodiments, sources 416 and 418 may communicate directly with user equipment devices 402, 404, and 406 via communication paths (not shown) such as those described above in connection with paths 408, 410, and 412.

Content source 416 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 416 may be the originator of content (e.g., a television broadcaster, a Webcast provider, etc.) or may not be the originator of content (e.g., an on-demand content provider, an Internet provider of content of broadcast programs for downloading, etc.). Content source 416 may include cable sources, satellite providers, on-demand providers, Internet providers, over-the-top content providers, or other providers of content. Content source 416 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 418 may provide media guidance data, such as the media guidance data described above. Media guidance application data may be provided to the user equipment devices using any suitable approach. In some embodiments, the guidance application may be a stand-alone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 418 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 418 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 418 may provide user equipment devices 402, 404, and 406 the media guidance application itself or software updates for the media guidance application.

Media guidance applications may be, for example, stand-alone applications implemented on user equipment devices. For example, the media guidance application may be implemented as software or a set of executable instructions which may be stored in storage 308, and executed by control circuitry 304 of a user equipment device 300. In some embodiments, media guidance applications may be client-server applications where only a client application resides on the user equipment device, and server application resides on a remote server. For example, media guidance applications may be implemented partially as a client application on control circuitry 304 of user equipment device 300 and partially on a remote server as a server application (e.g., media guidance data source 418) running on control circuitry of the remote server. When executed by control circuitry of the remote server (such as media guidance data source 418), the media guidance application may instruct the control circuitry to generate the guidance application displays and transmit the generated displays to the user equipment devices. The server application may instruct the control circuitry of the media guidance data source 418 to transmit data for storage on the user equipment. The client application may instruct control circuitry of the receiving user equipment to generate the guidance application displays.

Content and/or media guidance data delivered to user equipment devices 402, 404, and 406 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 400 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 4.

In one approach, user equipment devices may communicate with each other within a home network. User equipment devices can communicate with each other directly via short-range point-to-point communication schemes described above, via indirect paths through a hub or other similar device provided on a home network, or via communications network 414. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. patent application Ser. No. 11/179,410, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 416 to access content. Specifically, within a home, users of user television equipment 402 and user computer equipment 404 may access the media guidance application to navigate among and locate desirable content. Users may also access the media guidance application outside of the home using wireless user communications devices 406 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations that provide cloud-based services to various types of users and devices connected via a network such as the Internet via communications network 414. These cloud resources may include one or more content sources 416 and one or more media guidance data sources 418. In addition or in the alternative, the remote computing sites may include other user equipment devices, such as user television equipment 402, user computer equipment 404, and wireless user communications device 406. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 404 or wireless user communications device 406 having content capture feature. Alternatively, the user can first transfer the content to a user equipment device, such as user computer equipment 404. The user equipment device storing the content uploads the content to the cloud using a data transmission service on communications network 414. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 3.

Figure 5:
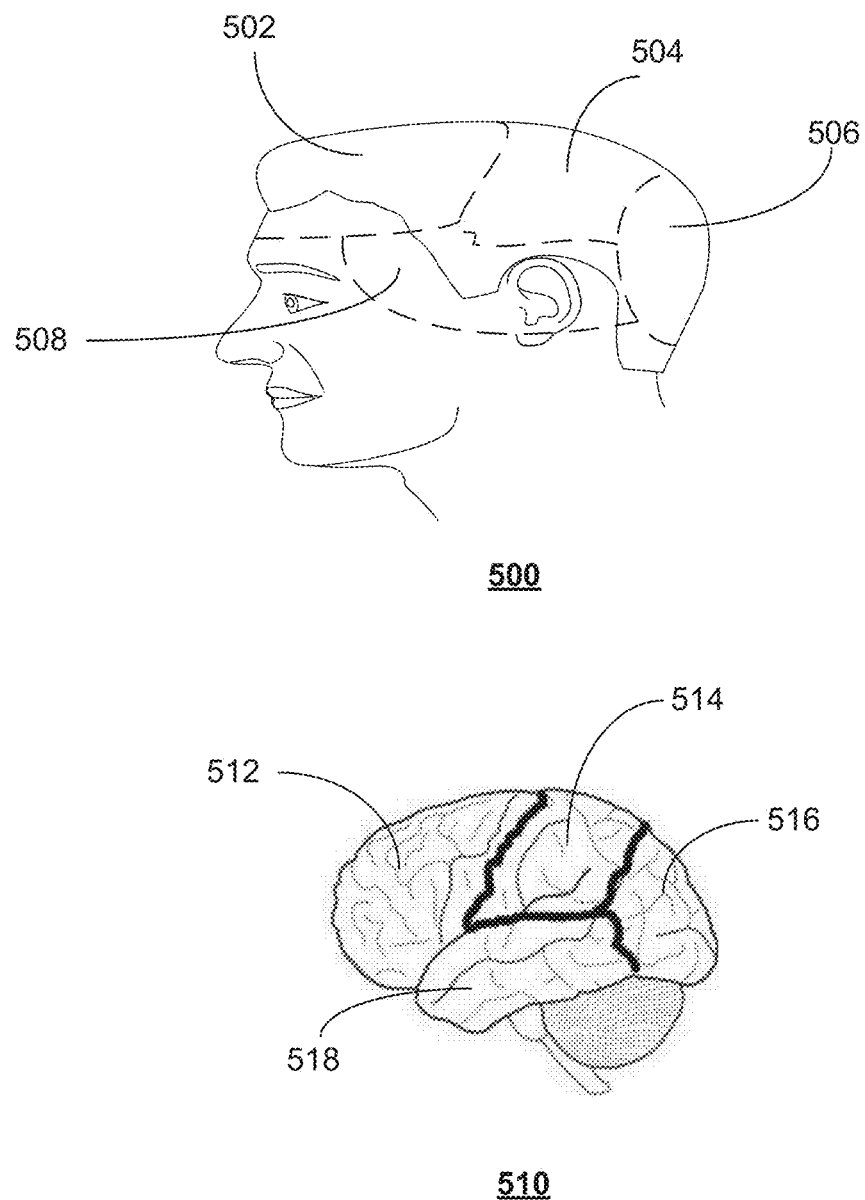
FIG. 5 shows a representation of a user and regions of the brain of the user associated with monitoring brain activity in accordance with some embodiments of the disclosure.

FIG. 5 shows a representation of a user and regions of the brain of the user associated with monitoring brain activity. For example, in some embodiments, the media guidance application may be implemented upon (or be in communication with) a user device that monitors brain activity of a user (e.g., via monitoring component 316 (FIG. 3)). The user device may reside upon the head of a user and include components (or sub-components) for testing different areas of the scalp of a user.

For example, the scalp of user 500 includes first portion 502, second portion 504, third portion 506, and fourth portion 508. In some embodiments, each of first portion 502, second portion 504, third portion 506, and fourth portion 508 may correspond to a different region of brain 510. For example, in some embodiments, first portion 502 may correspond to frontal lobe 512, second portion 504 may correspond to parietal lobe 514, third portion 506 may correspond to occipital lobe 516, and fourth portion 508 may correspond to temporal lobe 518.

For example, in some embodiments, the media guidance application may perform a media guidance application operation in response to brain activity detected in a particular region of the brain of a user. For example, the media guidance application may monitor brain activity of the user in portion 502 (e.g., using monitoring component 316 (FIG. 3)) and determine a first brain state associated with frontal lobe 512 of the monitored brain activity. The media guidance application may then cross-reference portion 502 with a database associated with functions performed by the user using regions of the brain to determine at least one function the user is performing based on the brain activity of the user in portion 502. For example, the cross-reference may reveal that frontal lobe 512 is associated with generating emotions and emotional responses in a user.

The media guidance application may then compare the first brain state to a threshold range for performing the at least one function, and in response to determining the first brain state does not correspond to the threshold range, performing a media guidance operation associated with the at least one function.

For example, the media guidance application may detect a state of the brain activity associated with frontal lobe 512 of the user. In response to determining that frontal lobe 512 is associated with emotions, the media guidance application of may compare the current brain state of the user to typical brain states (e.g., of the user or all users) associated with a particularly preferred emotion (e.g., happiness). In response to determining that the brain state of the user does not correspond to the preferred emotion (currently happy), the media guidance application may replace the media assets currently being consumed by the user with a media asset with a higher likelihood of making the user happy.

In another example, the media guidance application may detect a state of the brain activity associated with various regions of the brain in order to perform a function. For example, the media guidance application may detect a state of the brain activity associated with occipital lobe 516 (e.g., associated with vision) and parietal lobe 514 (e.g., associated with reading) of the user. In response to determining that the brain state of the brain activity associated with occipital lobe 516 (e.g., associated with vision) and parietal lobe 514 (e.g., associated with reading) of the user does not correspond to the typical brain state of a user, while temporal lobe 518 (e.g., associated with hearing) does correspond to the typical brain state of the user, the media guidance application may modify the media assets, display settings, etc. such that text or important events are communicated to the user via verbal means (e.g., audio announcements).

FIG. 6 shows multiple user devices that may be associated with monitoring brain activity. For example, a user device (e.g., upon which a media guidance application is implemented and/or which a media guidance application is in communication with) may be fashioned as a form of headwear.

For example, user device 600 is fashioned as a headset, user device 630 is fashioned as a hat/helmet, and user device 660 is fashioned as eye glasses. It should be noted that a user device configured to monitor brain activity as described herein may be fashioned as any headwear. Furthermore, in some embodiments, a user device may not be fashioned as headwear, but instead may be configured as any device capable of monitoring brain activity of a user. For example, any device which may incorporate and/or have access to an EEG, EMG, and/or other means for monitoring brain activity described herein may constitute a user device.

In some embodiments, user devices 600, 630, and 660 may further include additional sub-components (e.g., sub-components of monitoring component 316 (FIG. 3)), which may monitor brain activity on one or more regions of the brain. Sub-components may include electrodes or other features that may attach to the various portions (e.g., portions 502, 504, 506, and 508 (FIG. 5)) of a user (e.g., user 500 (FIG. 5)). Furthermore, in some embodiments, sub-components may extend and/or retract during various modes of the user device in order to accommodate the comfort of the user.

In some embodiments, user devices 600, 630, and 660 may be battery-powered in order to provide a user with additional mobility. Furthermore, user devices 600, 630, and 660 include multiple modes, each corresponding to different power consumption levels and/or sensitivity levels.

Figure 7:
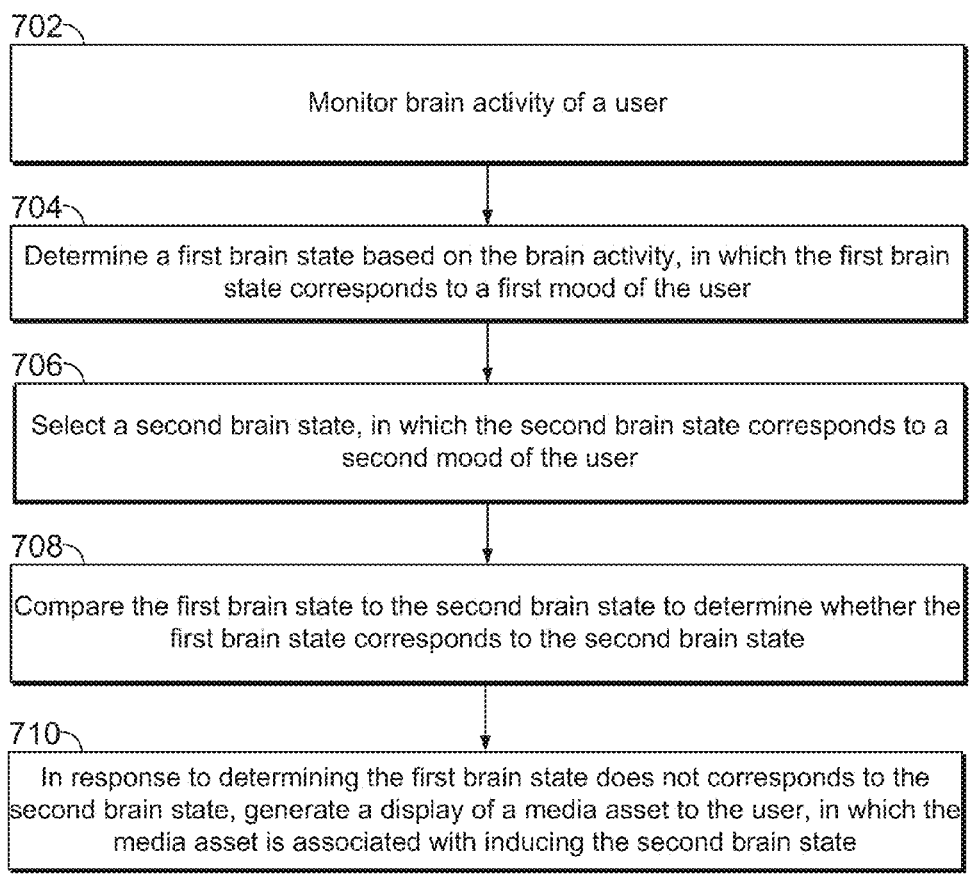
FIG. 7 is a flow-chart of illustrative steps involved in generating a media asset for display to a user, in which the media asset is associated with inducing a particular brain state in accordance with some embodiments of the disclosure.

FIG. 7 is a flow-chart of illustrative steps involved in generating a media asset for display to a user, in which the media asset is associated with inducing a particular brain state. It should be noted that process 700 or any step thereof, could be displayed on, or provided by, any of the devices shown in FIGS. 3-4 and 6 in response to brain activity of a user (e.g., user 500 (FIG. 5)). For example, process 700 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 700 may be incorporated into or combined with one or more steps of any other process (e.g., as described in FIGS. 8-18).

At step 702, the media guidance application monitors the brain activity of a user. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5)).

In some embodiments, the media guidance application may continuously monitor the brain activity of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input, (i.e., selecting selectable option 204 (FIG. 2)).

In some embodiments, the media guidance application may trigger (e.g., via control circuitry 304 (FIG. 3)) various modes for monitoring brain activity, in which each mode is associated with a different power consumption level and/or sensitivity level (e.g., as discussed below with regard to FIGS. 15-16). For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) in order to extend the life of an energy storage device or limit the exposure of a user (e.g., user 500 (FIG. 5) to activities of the monitoring component.

At step 704, the media guidance application determines a first brain state based on the brain activity, in which the first brain state corresponds to the mood of a user. For example, the media guidance application may receive data from a monitoring component (e.g., monitoring component 316 (FIG. 3)) incorporated into and/or in communication with (e.g., via communications network 414 (FIG. 4) a user device (e.g., user device 300 (FIG. 3) and/or user equipment device 402, 404, and/or 406 (FIG. 4)) upon which the media guidance application is implemented. The media guidance application may (e.g., via control circuitry 304 (FIG. 3)) process that data to determine a brain state that corresponds with the retrieved data. For example, the receiving data may correspond to a particular frequency range and/or electrical activity of the muscles near a particular region (e.g., frontal lobe 512 (FIG. 5)) of a brain (e.g., brain 510 (FIG. 5)) of the user.

The media guidance application may then cross-reference the frequency range of the brain activity of the user with a database stored locally on storage 308 (FIG. 3) or stored remotely at media guidance data source 418 (FIG. 4), and/or any location accessible via communications network 414 (FIG. 4)) associated with frequencies of brain states and corresponding moods to determine the first mood and/or cross-reference the electrical activity of the muscles near the brain of the user with a database (e.g., stored locally on storage 308 (FIG. 3) or stored remotely at media guidance data source 418 (FIG. 4), and/or any location accessible via communications network 414 (FIG. 4)) associated with electrical activity of brain states and corresponding moods to determine the a current mood of the user.

For example, the particular frequency range of the brain activity of a user may correspond to a particular mood (e.g., sadness). This correspondence may be recorded in a database, which records the various frequency ranges of different moods of the user and/or all users. To determine the correspondence, the media guidance application may input the determined frequency range of the brain activity of the user into the database. The database may then identify all available moods that correspond to the determined frequency range. For example, a brain state has a frequency of 4 to 8 Hz, the database may identify moods (e.g., happiness), corresponding to a frequency of 4 to 8 Hz. The database may then output the results, which indicate an identified mood that corresponds to the current frequency range of the brain activity of the user.

At step 706, the media guidance application selects a second brain state, in which the second brain state corresponds to a second mood of the user. In some embodiments, the media guidance application (e.g., via control circuitry 304 (FIG. 3)) may select the second brain state based on a current time, a user input, a current activity, or a preferred biorhythmic pattern associated with the user.

For example, the media guidance application may receive instructions from the user (e.g., entered via user input interface 310 (FIG. 3)) indicating that the user wishes to be in a particular mood (e.g., happy). Additionally or alternatively, the media guidance activity may retrieve a schedule (e.g., from storage 308 (FIG. 3)), which indicates that every evening at six o'clock PM, the user wishes to be in a happy mood.

In another example, the media guidance application may receive instructions from the user (e.g., via user input interface 310 (FIG. 3)) indicating that the user wishes to follow a particular schedule for his/her biorhythmic activity (e.g., the user wishes to maintain a therapeutic gradual increase and decrease in brain activity, frequency bands, etc.).

At step 708, the media guidance application compares the first brain state to the second brain state. In order to compare the different brain states, the media guidance application may retrieve quantitative measurements associated with each brain state. For example, in some embodiments, each brain state is associated with a particular frequency range, electrical activity, and/or threshold range. These quantitative measurements may be compared (e.g., using processing circuitry 306 (FIG. 3)) by the media guidance application to determine whether or not the two measurements match (e.g., within a particular degree of deviation). For example, the media guidance application may determine (e.g., via processing circuitry 306 (FIG. 3)) whether the two measurements share the same frequency bands.

At step 710, in response to determining the first brain state does not correspond to the second brain state, the media guidance application generates a display of a media asset to the user, in which the media asset is associated with inducing the second brain state. For example, in response to determining (e.g., via processing circuitry 306 (FIG. 3)) that the two quantitative measurements of brain activity do not match, the media guidance application may instruct (e.g., via control circuitry 304 (FIG. 3)) generate a display of a media asset associated with the second brain state. For example, in response to receiving instructions for a preferred mood (e.g., the second brain state), the media guidance application may ensure the user achieves that preferred mood by generating a display of a media asset that is associated with the preferred mood.

The media guidance application may (e.g., via processing circuitry 306 (FIG. 3)) process the second brain state to determine a corresponding media asset. For example, the media guidance application may cross-reference the second brain state with a database (e.g., stored locally on storage 308 (FIG. 3) or stored remotely at media guidance data source 418 (FIG. 4), and/or any location accessible via communications network 414 (FIG. 4)) associated with media assets corresponding to moods of a user to determine a media asset or a category of media assets associated with a particular mood. For example, the database may include data associated with each media asset indicating the particular mood or brain state that the media asset is associated with. Additionally or alternatively, a database may indicate every media asset associated with a particular mood or brain state. In order to select a particular media asset, the media guidance application (e.g., via control circuitry 304 (FIG. 3)) may identify the available media assets that corresponds to the second brain state.

In some embodiments, the information in the database may be generated by a third party. For example, the media guidance application may receive data associated with a media asset from a remote source (e.g., media content source 416 (FIG. 4)) that indicates the mood associated with the media asst. Additionally or alternatively, the media guidance application may track (e.g., via control circuitry 304 (FIG. 3)) the particular mood (e.g., as determined by data receiving from monitoring component 316 (FIG. 3)) that a user was in when the user viewed one or more previous showings of the media asset. The media guidance application may then associate that media asset with the particular mood.

After selecting the media asset, the media guidance application (e.g., via control circuitry 304 (FIG. 3) may transmit instructions to a display device (e.g., user equipment device 402, 404, and/or 406 (FIG. 4) and/or any display (e.g., display 312 (FIG. 3)) associated with the user device upon which the media guidance application is implemented and/or associated with to display the selected media asset (e.g., an inspiration message, preferred movie, etc.). The media guidance application may then monitor (e.g., using monitoring component 316 (FIG. 3)) the brain activity of the user to ensure that the second brain state is achieved. In response to determining that the second brain state is not achieved, the media guidance application may generate a display of a different media asset.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 7.

Figure 8:
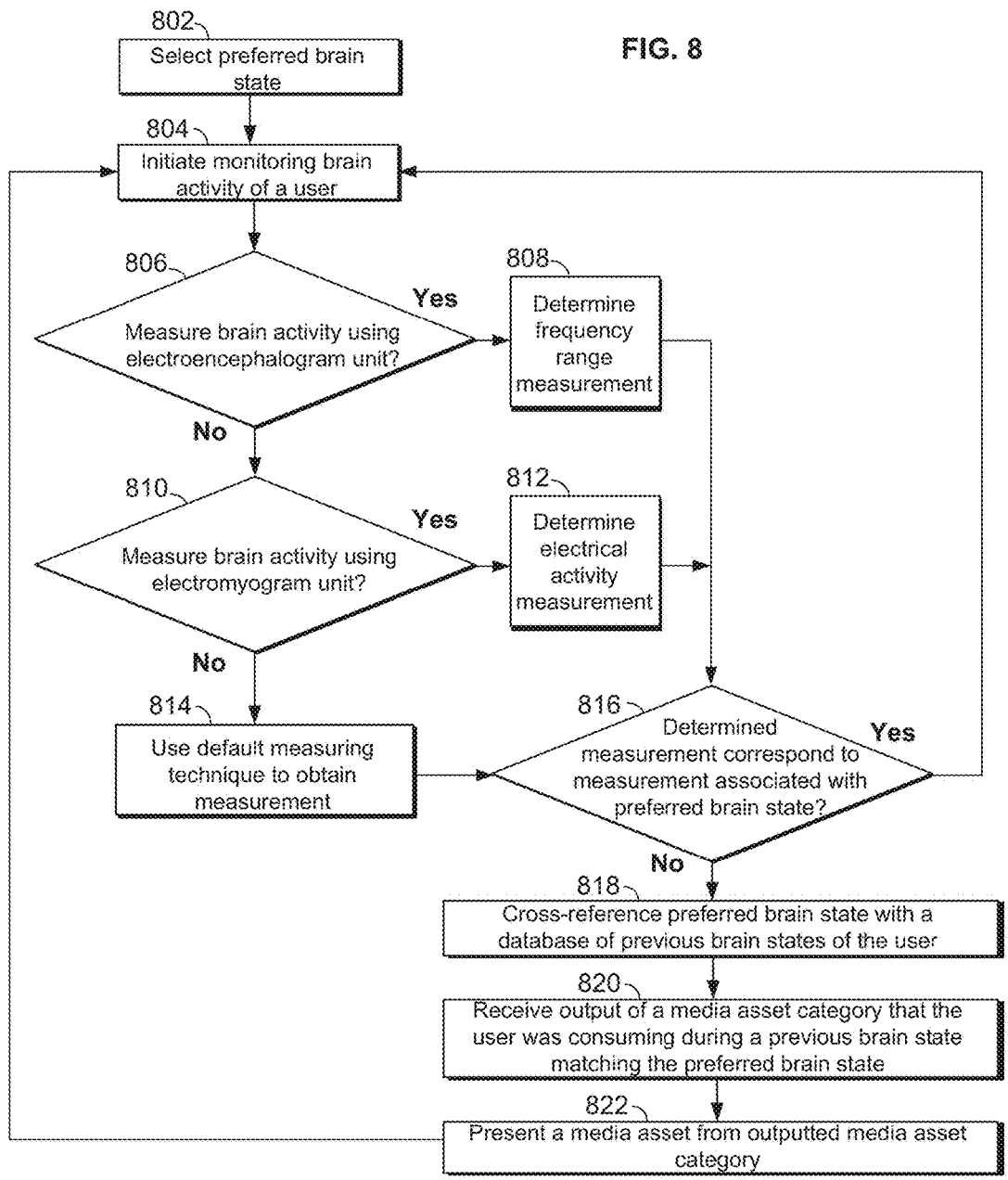
FIG. 8 is a flow-chart of illustrative steps involved in selecting a media asset associated with inducing a particular brain state in accordance with some embodiments of the disclosure.

FIG. 8 is a flow-chart of illustrative steps involved in selecting a media asset associated with inducing a particular brain state. It should be noted that process 800 or any step thereof, could be displayed on, or provided by, any of the devices shown in FIGS. 3-4 and 6 in response to brain activity of a user (e.g., user 500 (FIG. 5)). For example, process 800 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 800 may be incorporated into, or combined with, one or more steps of any other process (e.g., as described in FIGS. 7 and 9-18).

At step 802, the media guidance application selects a preferred brain state. The preferred state may be in response to a user selection (e.g., of one of selectable options 202 (FIG. 2)) indicating a particular mood the user would prefer to have. Additionally or alternatively, the media guidance application may receive instructions from the user (e.g., via user input interface 310 (FIG. 3)) indicating that the user wishes to have a particular scheduled brain state, or the media guidance application may receive (e.g., via I/O path 302 (FIG. 3)) a recommended brain state from a remote location (e.g., media content source 416, media guidance data source 418, and/or any location accessible via communications network 414 (FIG. 4)).

For example, the media guidance application may receive a user input indicating that the user wishes to be happy (or have a brain state corresponding to a brain state associated with happiness). In response the media guidance application may generate a display of media asset that may cause the user to become happy. Additionally or alternatively, the media guidance application may detect that a user is happy. In response the media guidance application may generate a display of media assets that are associated with happiness of the user. For example, in response to determining that a user is in a carefree mood (or has a brain state associated with carefreeness), the media guidance application may generate a display of comedies (or any other media asset associated with carefreeness). In contrast, in response to determining that a user is in a serious mood (or has a brain state associated with seriousness), the media guidance application may generate a display of documentaries (or any other media asset associated with seriousness).

At step 804, the media guidance application initiates monitoring of brain activity of a user. For example, the media guidance application (e.g., via control circuitry 304 (FIG. 3)) may instruct a user device (e.g., user device 600, 630, and/or 660 (FIG. 6)) to switch from a first mode associated with a first power consumption and/or sensitivity level to a second mode associated with a second power consumption and/or sensitivity level. For example, a first mode may be associated with a "stand-by" or "sleep" mode and may not include active monitoring of brain activity of a user. A second mode (e.g., an "active" mode) may include active monitoring of brain activity.

At step 806, the media guidance application determines whether or not to monitor the brain activity of a user using an EEG. For example, the user device (e.g., user device 600, 630, and/or 660 (FIG. 6)) may include one or more monitoring components (e.g., monitoring component 316 (FIG. 3)) or monitoring sub-components, which may include an EEG. If the media guidance application determines to monitor the brain activity of a user using an EEG, the media guidance application proceeds to step 808, determines a measurement of a frequency range of the brain activity of a user of one or more regions of the brain of a user, and then proceeds to step 816. If the media guidance application determines not to use an EEG (e.g., an EEG is not included in the monitoring component associated with the media guidance application), the media guidance application proceeds to step 810.

At step 810, the media guidance application determines whether or not to monitor the brain activity of a user using an EMG. For example, the user device (e.g., user device 600, 630, and/or 660 (FIG. 6)) may include one or more monitoring components (e.g., monitoring component 316 (FIG. 3)) or monitoring sub-components, which may include an EMG. If the media guidance application determines to monitor the brain activity of a user using an EMG, the media guidance application proceeds to step 812, determines a measurement of electrical activity of a user of one or more regions of the brain of a user, and then proceeds to step 816. If the media guidance application determines not to use an EMG (e.g., an EMG is not included in the monitoring component associated with the media guidance application), the media guidance application proceeds to step 812.

At step 814, the media guidance application determines whether or not to monitor the brain activity of a user using a default measuring technique. For example, the use device (e.g., user device 600, 630, and/or 660 (FIG. 6)) may include one or more monitoring components (e.g., monitoring component 316 (FIG. 3)) or monitoring sub-components, which may be configured for functional magnetic resonance imaging ("fMRI"), which tracks brain activity by monitoring the levels of oxygenated blood that travel to active neurons, a positron emission tomography scan ("PET scan"), which tracks neurons' use of glucose in response to a stimulus, or any other suitable technique. If the media guidance application determines to monitor the brain activity of a user using a default measuring technique, the media guidance application proceeds to step 816 and determines a measurement of the brain activity of a user of one or more regions of the brain of a user using the technique, and proceeds to step 816. It should be noted that, in some embodiments, the media guidance application may obtain one or more of the measurements using one or more techniques for monitoring brain activity.

At step 816, the media guidance application determines whether or not the measurement corresponds to measurement associated with preferred brain state. For example, in some embodiments, step 816 may correspond to step 708 (FIG. 7)). For example, in some embodiments, each brain state is associated with a particular frequency range, electrical activity, and/or threshold range. These quantitative measurements may be compared (e.g., using processing circuitry 306 (FIG. 3)) by the media guidance application to determine whether or not the two measurements match (e.g., within a particular degree of deviation). For example, the media guidance application may determine (e.g., via processing circuitry 306 (FIG. 3)) whether the two measurements share the same frequency bands.

If the media guidance application determines (e.g., via processing circuitry 306 (FIG. 3)) that the measurements do correspond, the media guidance application returns to step 804. If the media guidance application determines (e.g., via processing circuitry 306 (FIG. 3)) that the measurements do not correspond (e.g., the current brain state of the user is different than a preferred brain state of the user) the media guidance application proceeds to step 818.

At step 818, the media guidance application may (e.g., via control circuitry 304 (FIG. 3)) cross-reference the preferred brain state with a database of previous brain states of the user. For example, the media guidance application may search for a media asset (e.g., a movie, television program, video clip, textual message) that a user was watching when the user achieved the preferred brain state. For example, if the preferred brain state is happy, the media guidance application may search (e.g., via control circuitry 3 (FIG. 3)), for a media asset that previously made, or was previously viewed while, a user was happy (e.g., a humorous video clip).

In some embodiments, the database may be stored locally on storage 308 (FIG. 3) or stored remotely at media guidance data source 418 (FIG. 4) and/or any location accessible via communications network 414 (FIG. 4). Additionally or alternatively, the information in the database may be generated by a third party. For example, the media guidance application may receive data associated with a media asset from a remote source (e.g., media content source 416 (FIG. 4)) that indicates a mood associated with a media asset.

At step 820, the media guidance application receives an output of a media asset and/or a media asset category that the user was consuming during a previous brain state matching the preferred brain state. For example, if a movie of an Action genre previously made a user happy (e.g., the preferred brain state), the media guidance application may receive (e.g., via I/O path 302 (FIG. 3)) an output of an Action movie.

At step 822, the media guidance application presents a media asset from the outputted media asset category. For example, the media guidance application may generate a display (e.g., via instructions transmitted from control circuitry 304 FIG. 3)) of the outputted media asset on a display device (e.g., user equipment 402, 404, and/or 406 (FIG. 4)). After generating a display of the media asset from the outputted category, the media guidance application returns to step 804.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 8.

FIG. 9 is a flow-chart of illustrative steps involved in generating an icon associated with the brain activity of a user. It should be noted that process 900 or any step thereof, could be displayed on, or provided by, any of the devices shown in FIGS. 3-4 and 6 in response to brain activity of a user (e.g., user 500 (FIG. 5)). For example, process 900 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 900 may be incorporated into, or combined with, one or more steps of any other process (e.g., as described in FIGS. 7-8 and 10-18).

At step 902, the media guidance application monitors brain activity of a user for a first state in which the first state is associated with performing a first operation of a media guidance application. For example, in some embodiments, the media guidance application may perform various media guidance application operations based on a user achieving (or varying from) a particular brain state.

For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5))).

In some embodiments, the media guidance application may continuously monitor the brain activity of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input (e.g., selecting selectable option 204 (FIG. 2)).

In some embodiments, the media guidance application may trigger (e.g., via control circuitry 304 (FIG. 3)) various modes for monitoring brain activity, in which each mode is associated with a different power consumption level and/or sensitivity level (e.g., as discussed below with regard to FIGS. 15-16). For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) in order to extend the life of an energy storage device or limit the exposure of a user (e.g., user 500 (FIG. 5) to activities of the monitoring component. In some embodiments, the power consumption and/or sensitivity level may be associated with being monitored for a particular brain state. For example, if monitoring of the particular brain state requires a higher degree of sensitivity, the media guidance application (e.g., via control circuitry 304 (FIG. 3)) may instruct PMU 318 (FIG. 3) to switch to a mode corresponding to a higher level of sensitivity.

At step 904, the media guidance application generates for display an icon on a display screen, in which the icon provides feedback to the user related to achieving the first brain state. For example, as shown and described in FIGS. 1B-C, the media guidance application (e.g., via control circuitry 304 (FIG. 3)) may transmit instructions to generate a icon (e.g., icon 134, which may include graphical representations (e.g., graphical representation 132 (FIG. 1B)) and/or textual elements (e.g., textual element 138 (FIG. 1B)).

In some embodiments, an icon (e.g., icon 134 (FIG. 1B)) generated by a media guidance application (e.g., via control circuitry 304 (FIG. 4)) on a display (e.g., display 312 (FIG. 3) on a user device (e.g., user equipment device 402, 404, and/or 406 (FIG. 4)) may indicate the status of a first brain state and/or the progress of a user towards achieving a first brain state. Additionally or alternatively, the media guidance application may generate an icon (e.g., icon 134 (FIG. 1B) that includes instructions for achieving the first brain state and/or media guidance application operations that are associated with achieving (or not achieving) the first brain state.

At step 906, the media guidance application, in response to detecting a change in the brain activity of the user, adjusts the icon on the display screen to reflect the change in the brain activity. For example, as the media guidance application continuously, in response to user inputs, or periodically based on a predetermined schedule monitors the brain activity of a user using an EEG, EMG, or suitable device for monitoring brain waves (e.g., incorporated as a sub-component of monitoring component 316 (FIG. 3)), the media guidance application (e.g., via control circuitry 304 (FIG. 3)) may modify the generated icon (e.g., icon 134 (FIG. 1B)) to reflect the monitored brain activity. Accordingly, as a user's progress towards or away from a particular brain state (e.g., associated with a particular mood, attentiveness level, etc.) changes, the media guidance application present feedback to the user regarding the change.

It is contemplated that the steps or descriptions of FIG. 9 may be used with any other embodiment of this disclosure. In addition, the steps and descriptions described in relation to FIG. 9 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 9.

Figure 10:
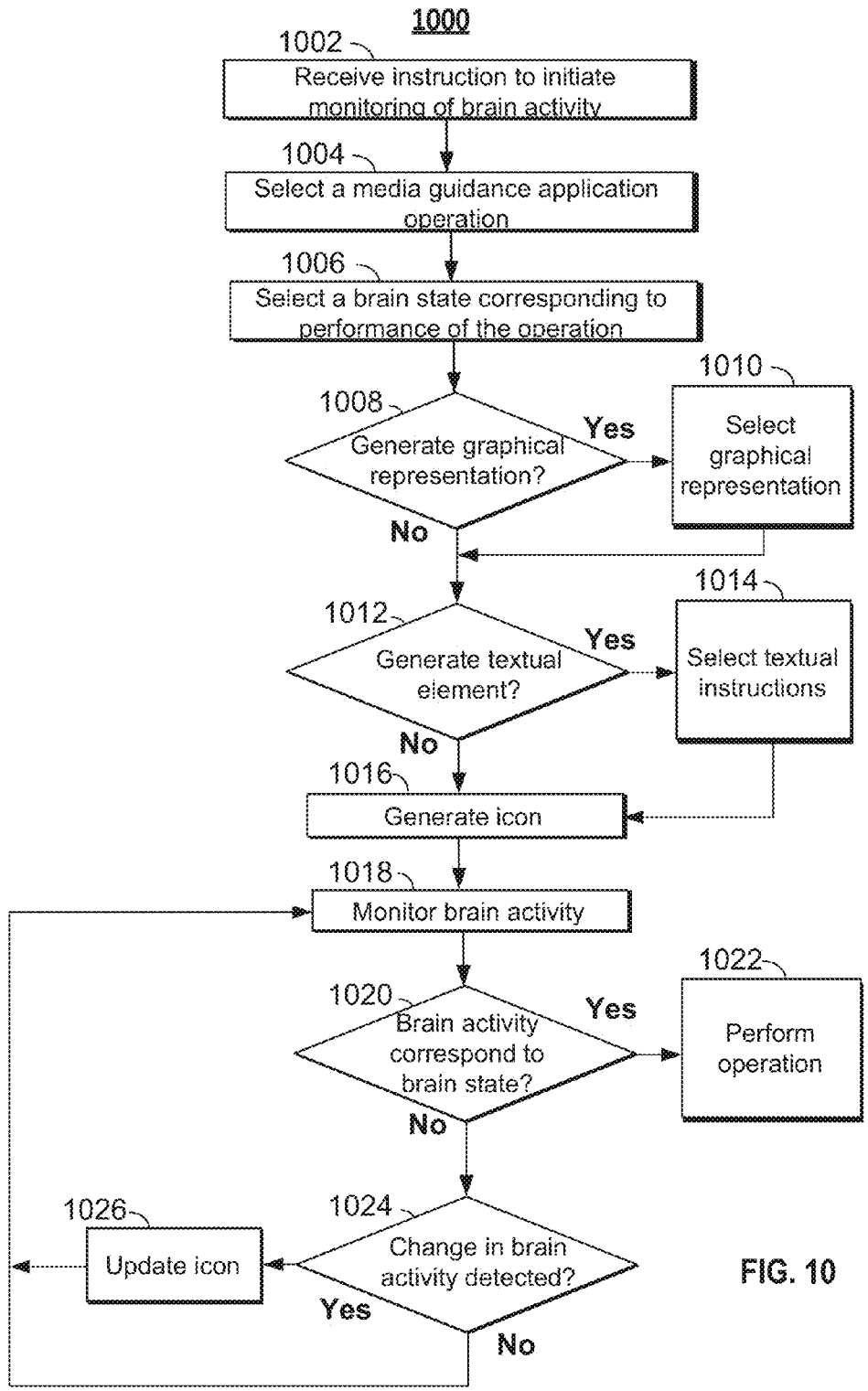
FIG. 10 is a flow-chart of illustrative steps involved in updating an icon associated with the brain activity of a user in accordance with some embodiments of the disclosure.

FIG. 10 is a flow-chart of illustrative steps involved in updating an icon associated with the brain activity of a user. It should be noted that process 1000 or any step thereof, could be displayed on, or provided by, any of the devices shown in FIGS. 3-4 and 6 in response to brain activity of a user (e.g., user 500 (FIG. 5)). For example, process 1000 may be executed by control circuitry 304 (FIG. 3) on user equipment devices 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1000 may be incorporated into, or combined with, one or more steps of any other process (e.g., as described in FIGS. 7-9 and 11-18).

At step 1002, the media guidance application receives an instruction to initiate monitoring of brain activity. For example, the media guidance application may receive a user input (e.g., via user input interface 310 (FIG. 3)) requesting the media guidance application to switch from a first mode (e.g., associated with limited brain activity monitoring and/or media guidance application operations) to a second more (e.g., associated with expansive brain activity monitoring and/or media guidance application operations).

At step 1004, the media guidance application selects a media guidance application operation to perform. For example, the media guidance application may be configured to perform one or more media guidance application operations while a user accesses media guidance (e.g., as shown and described in relation to FIGS. 1A-C). The media guidance application may select (e.g., via processing circuitry 306 (FIG. 3)) a media guidance application operation to perform. It should be noted, in some embodiments, the media guidance application may be configured to monitor for and/or perform multiple media guidance application operations simultaneously. However, for simplicity, only the performance of a single media guidance application operation will be discussed.

At step 1006, the media guidance application selects a brain state corresponding to performance of the media guidance application operation. For example, the media guidance application may retrieve (e.g., from storage 308 (FIG. 3)) a list of all media guidance application operations that the media guidance application is configured to perform. For each of those operations, the media guidance application may also retrieve a brain state, which, if detected (e.g., via monitoring component 316 (FIG. 3)), will cause the media guidance application to perform a particular media guidance application operation.

In some embodiments, the media guidance application may allow a user to customize the particular brain state that may trigger a particular media guidance application operation. Furthermore, the media guidance application may allow a user to calibrate brain state determination to a particular user and/or define the amount of time a user is given to achieve a particular brain state and well as the length of time a brain state must be maintained in order to perform a particular media guidance application operation. Any customization of a media guidance application may be stored (e.g., locally on storage 308 FIG. 3) or remotely on at any location accessible via communications network 414 (FIG. 4)) in a user profile associated with a user that is retrieve when a user active a user device (e.g., user device 600, 630, and/or 660 (FIG. 6)).

For example, a first media guidance application operation (e.g., a browse command) may be triggered in response to detecting that the attentiveness level of a user is below a threshold attentiveness level. A second media guidance application operation (e.g., selecting a currently highlighted media listing) may be triggered in response to determining the attentiveness level of a user is above a threshold attentiveness level. In another example, a third media guidance application operation (e.g., generating a display of an action movie) may be triggered in response to detecting that a user is in a particular mood. A fourth media guidance application operation (e.g., generating a display of a horror movie) may be triggered in response to determining the user is in a different mood.

At step 1008, the media guidance application determines whether or not to generate a graphical representation of progress of a user in achieving a brain state. For example, the media guidance application may determine (e.g., via processing circuitry 306 (FIG. 3)) whether or not to generate a display of a graphical representation (e.g., graphical representation 132 (FIG. 1B)) that indicates a user's progress in achieving a particular brain state, indicates a particular media guidance application operation that may be performed based on a user achieving a particular brain state, indicates how a user may achieve a particular brain state, and/or any other information associated with the media guidance application.

The media guidance application may generate any type of graphical representation. For example, the graphical representation may include any one or more animations, video clips, questionnaires, and/or any other graphical property used to convey information to a user. The data used to generate a graphical representation may be stored in a local (e.g., at storage 308 (FIG. 3)) or remote (e.g., as media content source 416, media guidance data source 418, and/or any location accessible via communications network 414 (FIG. 4)) location.

If the media guidance application determines not to generate a graphical representation, the media guidance application proceeds to step 1012. If the media guidance application determines to generate a graphical representation of the progress of a user to achieving the brain state, the media guidance application proceeds to step 1010 and selects a graphical representation corresponding to the brain state and the media guidance operation to be performed and then proceeds to step 1012. To select the graphical representation, the media guidance application may cross-reference the brain state and the media guidance operation to be performed in a database associated with various graphical representations. The database may be structured as a lookup table in which inputting the brain state and the media guidance operation to be performed may result in a graphical representation associated with the input being outputted.

At step 1012, the media guidance application determines whether or not to generate a textual element related to the progress of a user in achieving a brain state. For example, the media guidance application may determine (e.g., via processing circuitry 306 (FIG. 3)) whether or not to generate a display of a textual element (e.g., textual element 138 (FIG. 1B)) that relates to a user's progress in achieving a particular brain state, relates to a particular media guidance application operation that may be performed based on a user achieving a particular brain state, relates to how a user may achieve a particular brain state, and/or any other information associated with the media guidance application.

The media guidance application may generate any type of textual element. For example, a textual element may include any one or more font, character size, motion or animation, color, and/or any other graphical property used to convey information to a user as well as any content, including names, phrases, punctuation, etc. The data used to generate a textual element may be stored in local (e.g., at storage 308 (FIG. 3)) or remote (e.g., as media content source 416, media guidance data source 418, and/or any location accessible via communications network 414 (FIG. 4)).

If the media guidance application determines not to generate a textual element, the media guidance application proceeds to step 1012. If the media guidance application determines to generate a textual element, the media guidance application proceeds to step 1014 and selects a textual element corresponding to the brain state and media guidance operation to be performed and then proceeds to step 1012. To select the textual element, the media guidance application may cross-reference the brain state and the media guidance operation to be performed in a database associated with various textual elements. The database may be structured as a lookup table in which inputting the brain state and the media guidance operation to be performed may result in a textual element associated with the input being outputted.

At step 1016, the media guidance application generates an icon for display to the user incorporating the graphical representation and/or textual element (if any) selected. For example, the media guidance application may (e.g., via control circuitry 304 (FIG. 3)) generate an icon (e.g., icon 134 (FIG. 1B)) associated with a brain state, progress towards achieving a brain state, media guidance application operation to be performed, and/or any other information for display to a user (e.g., on display 312 (FIG. 3)).

The media guidance application may generate the icon (e.g., icon 134 (FIG. 1B)) as an overlay on a display (e.g., display 200 (FIG. 2)) generated by the media guidance application. Additionally or alternatively, the icon may appear in a separate window, on a separate user equipment device, in various shapes and sizes, and/or with various levels of transparency.

At step 1018, the media guidance application monitors the brain activity of the user. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5))).

In some embodiments, the media guidance application may continuously monitor the brain activity of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input (e.g., selecting selectable option 204 (FIG. 2)).

In some embodiments, the media guidance application may trigger (e.g., via control circuitry 304 (FIG. 3)) various modes for monitoring brain activity, in which each mode is associated with a different power consumption level and/or sensitivity level (e.g., as discussed below with regard to FIGS. 15-16). For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) in order to extend the life of an energy storage device or limit the exposure of a user (e.g., user 500 (FIG. 5) to activities of the monitoring component.

At step 1020, the media guidance application determines whether or not the brain activity of a user corresponds to the brain state. For example, the media guidance application may (e.g., via processing circuitry 306 (FIG. 3)) determine whether or not a frequency range associated with the brain state corresponds to the frequency range associated with the current brain state of the user. To determine the frequency range associated with the brain state, the media guidance application may cross-reference a database (e.g., at storage 308 (FIG. 3), media guidance data source 418 (FIG. 4), and/or any other location accessible via communications network 414 (FIG. 4)) associated with frequency ranges for various brain states.

If the media guidance application determines (e.g., via processing circuitry 306 (FIG. 3)) that the brain activity of the user corresponds to the brain state, the media guidance application (e.g., via control circuitry 304 (FIG. 3)) performs the media guidance application operation at step 1022. If the media guidance application determines (e.g., via processing circuitry 306 (FIG. 3)) that the brain activity of the user does not correspond to the brain state, the media guidance application (e.g., via control circuitry 304 (FIG. 3)) proceeds to step 1024.

At step 1024, the media guidance application determines (e.g., via monitoring component 316 (FIG. 3)) whether or not a change in the brain activity of the user is detected. If so, the media guidance application proceeds to step 1026 and updates the icon before returning to step 1018. If no change is detected, the media guidance application maintains the icon and returns to step 1018.

It is contemplated that the steps or descriptions of FIG. 10 may be used with any other embodiment of this disclosure. In addition, the steps and descriptions described in relation to FIG. 10 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 10.

Figure 11:
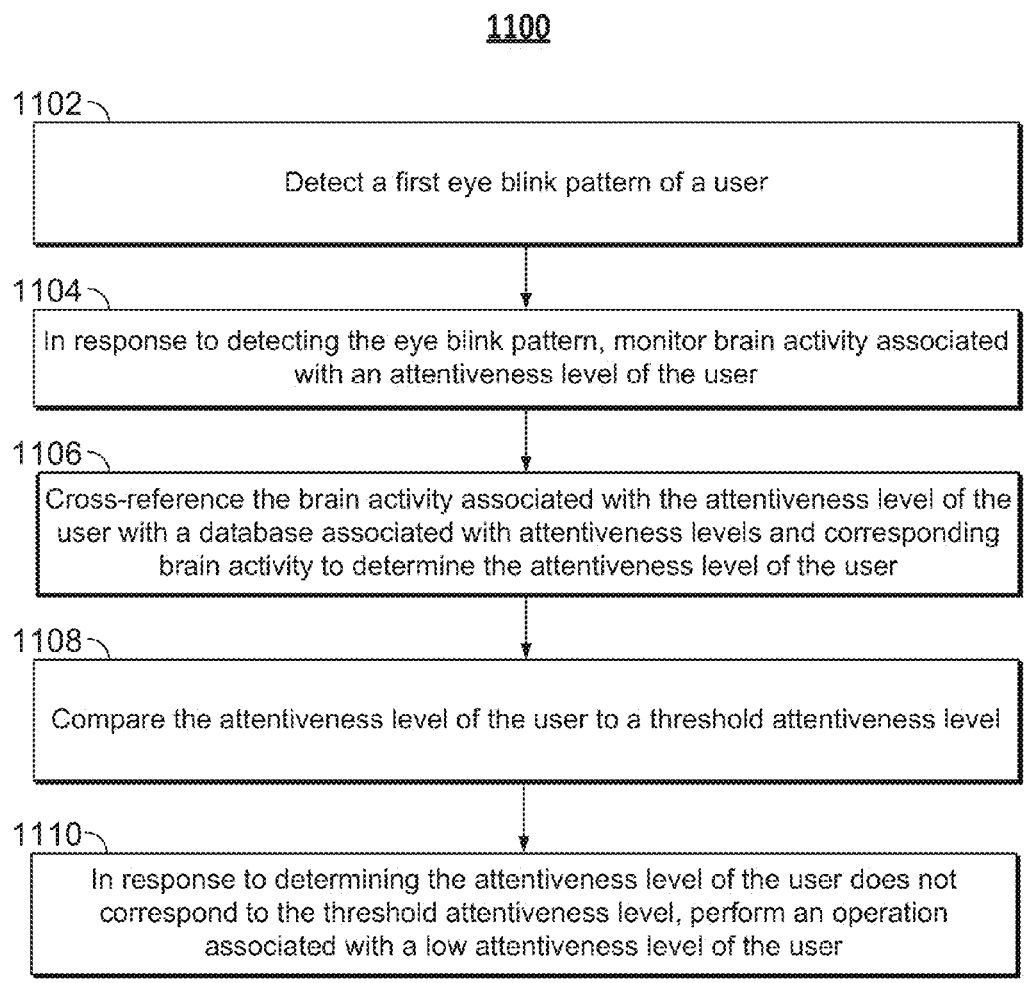
FIG. 11 is a flow-chart of illustrative steps involved performing an operation associated with a low attentiveness level of the user in accordance with some embodiments of the disclosure.

FIG. 11 is a flow-chart of illustrative steps involved performing an operation associated with a low attentiveness level of the user. It should be noted that process 1100 or any step thereof, could be displayed on, or provided by, any of the devices shown in FIGS. 3-4 and 6 in response to brain activity of a user (e.g., user 500 (FIG. 5)). For example, process 1100 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1100 may be incorporated into or combined with one or more steps of any other process (e.g. as described in FIGS. 7-10 and 12-18).

In some embodiments, the media guidance application may (e.g., via control circuitry 304 (FIG. 3)) perform one or more media guidance application and/or brain activity operations in response to detecting particular brain activity and/or determining a user has achieved a particular brain state. For example, in response to detecting a first type of brain activity, the media guidance application may monitor for a second type of brain activity. Process 1100 relates to determining the attentiveness level of a user and performing a browse operation in response to detecting a low attentiveness level of a user. It should be noted however that process 1100 may be equally applied to any brain activities and/or any media guidance application operation.

At step 1102, the media guidance application detects a first eye blink pattern of a user. In some embodiments, the media guidance application may be configured to detect particular eye blink patterns while monitoring the brain activity of a user. For example, the media guidance application (e.g., via monitoring component 316 (FIG. 3)) may monitor alpha bands (e.g., typically associated with eye blinking) in the globus pallidus of the basal ganglia (e.g., the area of the brain typically associated with controlling eye blinking) of a user (e.g., user 500 (FIG. 5)) in order to detect an eye blink pattern.

At step 1104, the media guidance application may in response to detecting the eye blink pattern, monitor brain activity associated with an attentiveness level of the user. For example, in response to detecting a first type of brain activity (e.g., an eye blink pattern), the media guidance application initiates the monitoring (e.g., via monitoring component 316 (FIG. 3)) of a second type of brain activity of a user (e.g., user 500 (FIG. 5)). In this example, in response to detecting the first eye blink pattern, the media guidance application monitors the brain activity associated with the attentiveness of a user.

For example, as described in relation to FIG. 2, the media guidance application may (e.g., control circuitry 304 (FIG. 3)) generate a display of a media asset and/or media guidance data (e.g., as shown in display 200 (FIG. 2)) on a display screen (e.g., associated with user device 402, 404, and/or 406 (FIG. 4)) in which a user may navigate through various media guidance application operations using a first type of brain activity (e.g., associated with the first eye blink pattern). Upon detecting a second eye blink pattern, the media guidance application may (e.g., via control circuitry 304 (FIG. 3)) select a media guidance application operation to perform as well as a brain activity that may trigger the selected media guidance application operation. Following the selection, the media guidance application (e.g., via monitoring component 316 (FIG. 3)) monitors for a different type of brain activity. In process 1100, the media guidance application (e.g., via monitoring component 316 (FIG. 3)) monitors for brain activity associated with the attentiveness of a user.

For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5))) in the region of the brain (e.g., portion 502, 504, 506, and/or 508 (FIG. 5)) associated with attentiveness of a user.

In some embodiments, the media guidance application may also transmit (e.g., via control circuitry 304 (FIG. 3)) an instruction to switch to a particular mode associated with monitoring for brain activity associated with an attentiveness level of a user. For example, a user device (e.g., user device 600, 630, and/or 660 may have a particular power consumption level and/or sensitivity level (e.g., as discussed below with regard to FIGS. 15-16) associated with monitoring for an attentiveness level of a user.

At step 1106, the media guidance application may cross-reference the brain activity of the user with a database associated with attentiveness levels of brain states to determine an attentiveness level of the user. For example, the media guidance application may (e.g., via control circuitry 304 (FIG. 3)) input the frequency range of brain activity of a user, the electrical activity of muscles near brain of the user at rest and during contraction, etc. into a database (e.g., stored locally of storage 308 (FIG. 3) or stored remotely at any location accessible via communications network 414 (FIG. 4)) and receive a description of the attentiveness of the user.

At step 1108, the media guidance application compares the attentiveness level of the user to a threshold attentiveness level. For example, the media guidance application may receive the attentiveness level of the user in the same unit of measure as a threshold attentiveness level. In some embodiments, a threshold attentiveness level may be retrieved from local storage (e.g., storage 308 (FIG. 3)). Alternatively, a threshold attentiveness level may be received (e.g., via I/O path 302 (FIG. 3)) from a remote location (e.g., any location accessible via communications network 414 (FIG. 4)). Additionally, the threshold attentiveness level may also be customized based on a user. For example, some users may normally have higher or lower attentiveness levels when consuming media.

The media guidance application may then (e.g., via processing circuitry 306 (FIG. 3)) determine whether or not the attentiveness level of the user corresponds to the threshold attentiveness level at step 1110. At step 1110, the media guidance application, in response to determining the attentiveness level of the user does not correspond to the threshold attentiveness level, performs an operation associated with a low attentiveness level. For example, if the media guidance application determines that a user is not currently paying attention to a media asset displayed on a display device (e.g., user equipment device 402, 404, and/or 406 (FIG. 4)), the media guidance application may (e.g., via control circuitry 304 (FIG. 3)) perform a browse function (e.g., scroll from one media object generated for display in a media guide to another media object generated for display in a media guide).

In some embodiments, the media guidance application operation associated with brain states may be determined based on instructions received from storage 308 (FIG. 3). Alternatively or additionally, the media guidance application (e.g., implemented on user device 300 (FIG. 3)) may receive instructions for a particular media guidance application operation to perform based on particular brain activity from remote sources (e.g., any location accessible via communications network 414 (FIG. 4). The media guidance application may also receive user input (e.g., via user input interface 310 (FIG. 3)) customizing the media guidance application operation performed.

In some embodiments, monitoring component 316 (FIG. 3) may be coupled to an Infrared (IR) Blaster or Emitter (e.g., incorporated in and/or accessible to control circuitry 304 (FIG. 3)). A person may tune to a channel using a media guidance application that operates based on the output of monitoring component 316 (FIG. 3). For example, the media guidance application may receive output from monitoring component 316 (FIG. 3) indicating EEG measurements for "attention" and "blink". Using that information, the media guidance application may change channels and/or select content in the media guidance application.

In some embodiments, the media guidance application may utilize a blink detection output from monitoring component 316 (FIG. 3) to initiate a grid display. For example, monitoring component 316 (FIG. 3) may output a blink detection of the user which may instruct the media guidance application to launch a grid display (e.g., display 100 (FIG. 1A), display 200 (FIG. 2), etc.). Based on data received from monitoring component 316 (FIG. 3), the media guidance application (e.g., via control circuitry 304 (FIG. 3)) may transmit a series of IR commands or wireless commands in response to detecting a blink instructing the media guidance application to display a list of favorite channels or a grid (e.g., grid 102 matching a user's preferences).

It should be noted, although grid navigation is discussed below, any other type of user interface or media guidance display may be navigated to select content in a similar way. For example, an online website or application on a mobile device may present media listings in a similar manner as the media guidance display shown in display 100 (FIG. 1A), display 200 (FIG. 2), etc. The media guidance display may be navigated up/down/left/right to identify content for selection in a similar way as discussed below.

The media guidance application (e.g., via control circuitry 304 (FIG. 3)) may transmit an "Arrow Down" command at a rate of about one command per second until monitoring component 316 (FIG. 3) detects another "blink" from the user. Specifically, the grid shown in display 100 (FIG. 1A), display 200 (FIG. 2), etc. may be scrolled left/right/up/down at a constant rate automatically until the user blinks a second time. For example, when the user blinks the first time, the media guidance application may be instructed to launch a grid. Until a subsequent blink is detected (e.g., a second time the user blinks), the grid that is displayed may be scrolled to display additional content sources (e.g., channels) using the down arrow 120 (FIG. 1A) automatically at a constant rate of one content source per second. Alternatively, until a subsequent blink is detected (e.g., a second time the user blinks), the grid that is displayed may be scrolled to display later/earlier using the right arrow 120 automatically at a constant rate of thirty minute intervals per second.

In some embodiments, after the second blink is detected or after another mental/physical condition is detected by monitoring component 316 (FIG. 3), attention of the user is monitored. In some implementations, monitoring component 316 (FIG. 3) may wait a threshold period of time (e.g., five seconds) for the attention level to increase. For example, after the grid is scrolled to a specific position (e.g., time and content source list), monitoring component 316 (FIG. 3) may measure an attention level of the user by analyzing brain wave frequencies. Monitoring component 316 (FIG. 3) may compare the brain state before the second blink and/or other mental/physical condition was detected and the brain state after the second blink and/or other mental/physical condition was detected.

Specifically, monitoring component 316 (FIG. 3) may compare the previous brain states (e.g., those occurring while the grid was being scrolled) to those occurring after the grid has stopped scrolling. If the brain state has changed beyond a threshold range, monitoring component 316 (FIG. 3) may output an indication that the user attention level has increased. In some implementations, monitoring component 316 (FIG. 3) may compare the current brain state frequencies to a threshold range to determine whether the user attention level has increased or reached a threshold range associated with a particular mood, attentiveness level, etc. For example, monitoring component 316 (FIG. 3) may wait until the brain state of the user reaches a brain state associated with a 60% attentiveness level. Upon determining that that brain state has been reached, monitoring component 316 (FIG. 3) may output an indication that the user attentiveness level has increased.

In some implementations, once monitoring component 316 (FIG. 3) outputs the indication that the user attentiveness level has increased, monitoring component 316 (FIG. 3) may generate an instruction to the media guidance application to select the content source shown in the grid. For example, monitoring component 316 (FIG. 3) may instruct the media guidance application to tune to the current channel identified by a highlight region in grid 102 (FIG. 1A). In some implementations, when multiple content sources are shown in the media guidance application display, upon determining that the user attention level has increased, an eye position detection module (e.g., incorporated into monitoring component 316 (FIG. 3)) may determine where the user's eyes are focused. Specifically, the eye position detection module may identify to the media guidance application where the user's eyes are focused when the user attentiveness level has increased. The media guidance application may correlate that information with which content source is shown at the position being focused by the user's eyes. The media guidance application may then tune or access the content source the user is focusing on when the user attention level has increased as determined by monitoring component 316 (FIG. 3).

In some implementations, monitoring component 316 (FIG. 3) may determine whether, after the threshold period of time (e.g., five seconds), the attentiveness level has not increased following the second blink detection or after another mental/physical condition is detected. In response to determining that the attentiveness level has not increased after the threshold period of time, monitoring component 316 (FIG. 3) may instruct the media guidance application to scroll again (e.g., the time or content source or both) at a given rate (e.g., once per second). Specifically, monitoring component 316 (FIG. 3) may transmit an "Arrow Down" command at a rate of about one command per second until monitoring component 316 (FIG. 3) detects another "blink" from the user (e.g., a third blink). Specifically, the grid shown in display 100 or 200 may be scrolled left/right/up/down at a constant rate automatically until the user blinks a third time. Until the third blink is detected (e.g., a second time the user blinks), the grid that is displayed may be scrolled to display additional content sources (e.g., channels) using the down arrow 120 automatically at a constant rate of one content source per second.

Alternatively, until the third blink is detected (e.g., a second time the user blinks), the grid that is displayed may be scrolled to display later/earlier using the right arrow 120 automatically at a constant rate of thirty minute intervals per second. Monitoring component 316 (FIG. 3) may then repeat the process of determining whether the attentiveness level of the user has increased to instruct the media guidance application to select a given content source.

In some embodiments, the media guidance application may recommend a media asset based on a current or desired mental state of the user. Specifically, based on a measured brain state of the user monitoring component 316 (FIG. 3) may inform the media guidance application of the user's current or desired brain state. The media guidance application may then automatically select a media asset to match the current or desired mental state. For example, the user may be in a happy state of mind as determined by monitoring component 316 (FIG. 3). Monitoring component 316 (FIG. 3) may inform the media guidance application that the user is happy and the media guidance application may select media asset that correspond to that state of mind (e.g., comedy media assets). For example, the user may desire to be in a sad state of mind as determined by monitoring component 316 (FIG. 3). Monitoring component 316 (FIG. 3) may inform the media guidance application that the user desires to be sad and the media guidance application may select media asset that correspond to that state of mind (e.g., drama media assets).

Monitoring component 316 (FIG. 3) may record the brain states of a user for a period of time that the user is experiencing a media asset. After recording the brain states while experiencing many media assets, the media guidance application (e.g., via processing circuitry 306 (FIG. 3)) may generate correlations with different media characteristics or attributes, such as genre, actors, content sources and other metadata. For example, the media guidance application (e.g., via processing circuitry 306 (FIG. 3)) may determine that the user is usually (e.g., more than 60-80 percent or greater than a threshold amount of time) in a sleep state of mind when watching comedies. Accordingly, the media guidance application (e.g., via processing circuitry 306 (FIG. 3)) may correlate comedies with a sleep state of mind. Based on these correlations, media guidance application (e.g., via processing circuitry 306 (FIG. 3)) may determine a current state of mind and find a media asset to match the current state of mind. Specifically, if the correlation determines that when the user is in a sleepy state of mind, the user watches comedy type media assets, media guidance application (e.g., via control circuitry 304 (FIG. 3)) may select a comedy media asset when the user is determined to be currently in a sleep state of mind.

In some implementations, the recommended media assets may be selected to place the user in a desired state of mind. For example, the user may instruct the media guidance application of the desire to enter a sleepy state of mind. The media guidance application may cross-reference the correlations generated by monitoring component 316 (FIG. 3)) to determine what types of media assets are correlated with the sleepy state of mind for the user. The correlations may indicate that comedies are associated with a sleepy state of mind. Accordingly, the media guidance application may select a comedy media asset to cause the user to enter the state of mind (e.g., sleepy) selected by the user. This way a user who is in an active state can tell the media application they want to enter a sleepy state. Based on past brain activity detected for the user by monitoring component 316 (FIG. 3)), the media guidance application may determine the types of media assets the user needs to consume to enter the desired state of mind (e.g., sleepy).

In some embodiments, the information received from monitoring component 316 (FIG. 3) may be used to select which advertisements to deliver to the device or user connected to monitoring component 316 (FIG. 3). For example, monitoring component 316 (FIG. 3) may receive an indication from the media guidance application that an advertisement needs to be displayed. Monitoring component 316 (FIG. 3) may measure brain states of the user to determine a state the user is in. Monitoring component 316 (FIG. 3) may inform the media guidance application about the determined state of the user. The media guidance application, based on the determined state (e.g., sleepy state), may select an advertisement suitable for the state. For example, the media guidance application may select an advertisement about a bed when the user is in a sleepy state as determined by monitoring component 316 (FIG. 3). Alternatively, the media guidance application may select an advertisement about baseball game when the user is in an active state as determined by monitoring component 316 (FIG. 3).

In some embodiments, monitoring component 316 (FIG. 3) may monitor user reactions to the displayed advertisements. Monitoring component 316 (FIG. 3) may determine when the user attentiveness level rises when an advertisement is displayed. For example, the media guidance application may determine that an advertisement is being displayed. In response, the media guidance application may instruct monitoring component 316 (FIG. 3) to monitor the frequencies of the user to determine whether the attentiveness level of the user has increased. Specifically, monitoring component 316 (FIG. 3) may determine whether the brain activity increased between the time prior to when the advertisement was displayed and when the advertisement was shown. When the brain activity is determined to have increased, monitoring component 316 (FIG. 3) may indicate that the attention level of the user increased when the advertisement was displayed. Alternatively or in addition, monitoring component 316 (FIG. 3) may measure the brain frequencies at the time the advertisement is displayed. When the brain frequencies rise above a given threshold, monitoring component 316 (FIG. 3) may indicate that the attention level of the user increased when the advertisement was displayed. Based on the indications received from monitoring component 316 (FIG. 3) the media guidance application may determine which advertisements have the greatest impact or affect on the user (e.g., which advertisements caused the user's attention level to increase). The media guidance application may adjust a user profile based on the determination to improve the advertisement targeting/selection in the future.

It is contemplated that the steps or descriptions of FIG. 11 may be used with any other embodiment of this disclosure. In addition, the steps and descriptions described in relation to FIG. 11 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 11.

Figure 12:
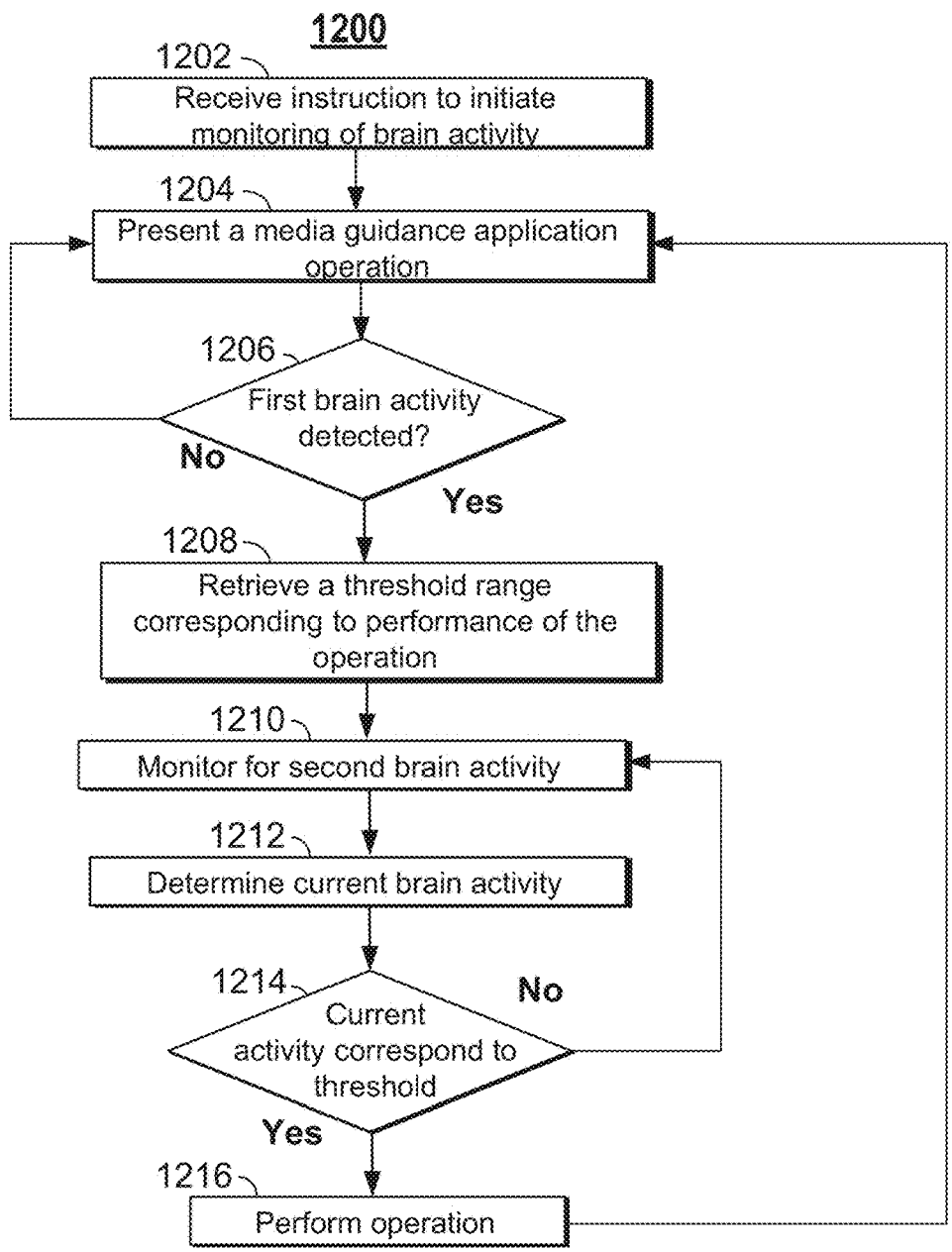
FIG. 12 is a flow-chart of illustrative steps involved in detecting and responding to various types of brain activity in accordance with some embodiments of the disclosure.

FIG. 12 is a flow-chart of illustrative steps involved in detecting and responding to various types of brain activity. It should be noted that process 1200 or any step thereof, could be displayed on, or provided by, any of the devices shown in FIGS. 3-4 and 6 in response to brain activity of a user (e.g., user 500 (FIG. 5)). For example, process 1200 may be executed by control circuitry 304 (FIG. 3), on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1200 may be incorporated into or combined with one or more steps of any other process (e.g. as described in FIGS. 7-11 and 13-18).

At step 1202, the media guidance application receives instructions to initiate monitoring of brain activity. For example, the media guidance application may receive a user input (e.g., via user input interface 310 (FIG. 3)) requesting the media guidance application to switch from a first mode (e.g., associated with limited brain activity monitoring and/or media guidance application operations) to a second mode (e.g., associated with associated with expansive brain activity monitoring and/or media guidance application operations). For example, a user may have selected selectable option 204 (FIG. 2) instructing a user device (e.g., user device 600, 630, and/or 660 (FIG. 6)) to actively monitor the brain activity of the user.

At step 1204, the media guidance application may present a media guidance application operation. For example, the media guidance application may present a display of an icon (e.g., icon 218 (FIG. 2)) on a display screen (e.g., display 200 FIG. 2)) on a user device (e.g., user equipment device 402, 404, and/or 406 (FIG. 4)), which instructs a user regarding the monitoring of brain activity. For example, the icon (e.g., icon 218 (FIG. 2)) may instruct a user to blink his/her eyes in order to scroll the different media guidance application operations that are available.

At step 1206, the media guidance application determines whether or not a first brain activity is detected. For example, the media guidance application may monitor the brain activity of a user for a particular type of brain activity. For example, the media guidance application may (e.g., via monitoring component 316 (FIG. 3)) monitor a particular region of the brain (e.g., portion 502, 504, 506, and/or 508 (FIG. 5)) for a particular type of brain activity (e.g., a particular frequency range, frequency band, electrical activity, etc.). In some embodiments, step 1206 may correspond to step 1102 (FIG. 11), and the media guidance application may be configured to detect particular eye blink patterns while monitoring the brain activity of a user. For example, the media guidance application (e.g., via monitoring component 316 (FIG. 3)) may monitor alpha bands (e.g., typically associated with eye blinking) in the globus pallidus of the basal ganglia (e.g., the area of the brain typically associated with controlling eye blinking) of a user (e.g., user 500 (FIG. 5)) in order to detect an eye blink pattern.

If the media guidance application determines that first brain activity is not detected, the media guidance application returns to step 1204. If the media guidance application determines that the first brain activity is detected, the media guidance application proceeds to step 1208 and retrieves a threshold range necessary for performance of the operation. For example, the media guidance application may retrieve a threshold range, which if detected triggers performance of the media guidance application operation. The threshold range may be, depending on the user (e.g., based on information in a user profile), based on the particular media guidance application operation to be performed (e.g., each operation may be associated with a unique threshold range), based on information received from a remote source (e.g., an industry standard threshold range), etc.

At step 1210, the media guidance application monitors the brain activity of a user. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5)).

In some embodiments, the media guidance application may continuously monitor the brain activity of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input (e.g., selecting selectable option 204 (FIG. 2)).

In some embodiments, the media guidance application may trigger (e.g., via control circuitry 304 (FIG. 3)) various modes for monitoring brain activity, in which each mode is associated with a different power consumption level and/or sensitivity level (e.g., as discussed below with regard to FIGS. 15-16). For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)). In some embodiments, particular modes may be invoked in order to monitor for particular brain activity and/or in order to monitor particular regions (e.g., portion 502, 504, 506, and/or 508 (FIG. 5)) of the brain (e.g., brain 550 (FIG. 5)).

At step 1212, the media guidance application determines the current brain activity of the user. For example, the media guidance application may determine a particular frequency range, frequency band, etc. of the current brain activity of the user. At step 1214, the media guidance application determines whether or not the current brain activity corresponds to the threshold brain activity. For example, the media guidance application may determine (e.g., via processing circuitry 306 (FIG. 3)) whether the current brain activity of a user (e.g., indicative of an attentiveness level of the user) corresponds to a threshold range (e.g., indicative of an attentiveness level necessary to perform a media guidance application operation). If the media guidance application determines that the current brain activity does not correspond to the threshold brain activity, the media guidance application returns to step 1210. If the media guidance application determines that the current brain activity does correspond to the threshold brain activity, the media guidance application proceeds to step 1216.

At step 1216, the media guidance application performs the media guidance application operation. For example, if the media guidance application operation is the recommendation of media assets, the media guidance application may, in response to determining the user is unhappy (e.g., the current brain activity of the user does not meet a threshold range associated with happiness) with a current media asset (e.g., displayed on user equipment 402, 404, and/or 406 (FIG. 4)), recommend different media assets.

The media guidance application then returns to step 1204. For example, the media guidance application may return to step 1204 and present a media guidance application operation corresponding to stopping the media guidance application operation performed in step 1216 (e.g., stopping the recommendation of media assets).

It is contemplated that the steps or descriptions of FIG. 12 may be used with any other embodiment of this disclosure. In addition, the steps and descriptions described in relation to FIG. 12 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one or more of the steps in FIG. 12.

Figure 13:
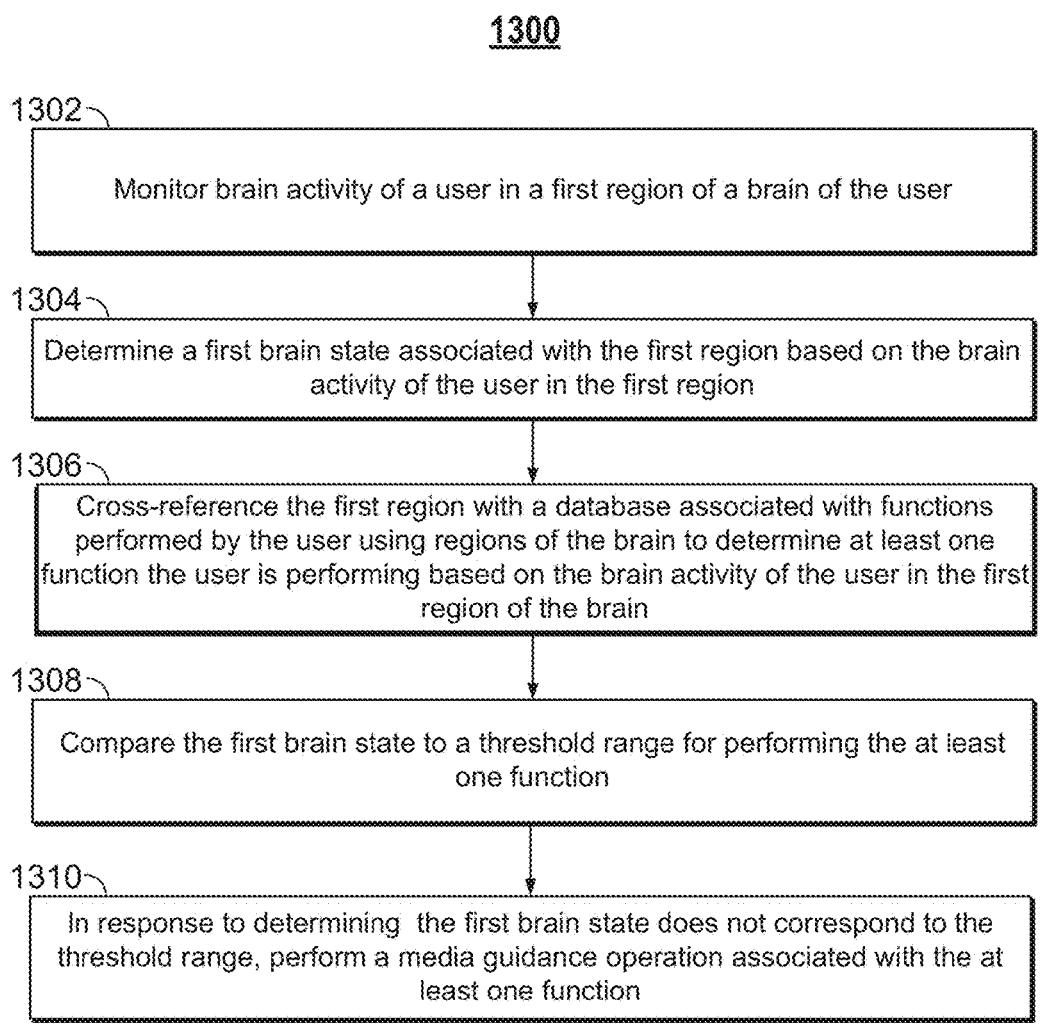
FIG. 13 is a flow-chart of illustrative steps involved in monitoring particular regions of a brain for brain activity associated with particular functions in accordance with some embodiments of the disclosure.

FIG. 13 is a flow-chart of illustrative steps involved in monitoring particular regions of a brain for brain activity associated with particular functions. It should be noted that process 1300 or any step thereof, could be provided by, any of the devices shown in FIGS. 3-4 and 6 in response to brain activity of a user (e.g., user 500 (FIG. 5)). For example, process 1300 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1300 may be incorporated into or combined with one or more steps of any other process (e.g. as described in FIGS. 7-12 and 14-18).

At step 1302, the media guidance application monitors brain activity of a user in a first region of a brain of the user. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a region (e.g., portion 502, 504, 506, and/or 508 (FIG. 5)) of a brain (e.g., brain 510 (FIG. 5)) of a user (e.g., user 500 (FIG. 5)).

In some embodiments, the media guidance application may continuously monitor the brain activity at different regions of the brain of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input (e.g., selecting selectable option 204 (FIG. 2)). In some embodiments, the media guidance application may (e.g., via monitoring component 316 (FIG. 3)) receive data from various electrodes located at various regions on the scalp of a user. In some embodiments, the various electrodes may extend and/or retract from a user device (e.g., user device 600, 630, and/or 660 (FIG. 6)).

In some embodiments, the media guidance application may trigger (e.g., via control circuitry 304 (FIG. 3)) various modes for monitoring brain activity, in which each mode is associated with a different power consumption level and/or sensitivity level (e.g., as discussed below with regard to FIGS. 15-16). For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) based on a particular region of a brain of the user that needs to be monitored. For example, if the region of the brain is more difficult to monitor due to location, density, size/shape of the user device, etc., the media guidance application may adjust the power consumption and/or sensitivity level accordingly.

At step 1304, the media guidance application determines a first brain state associated with a first region of the brain based on the brain activity of the user in the first region. For example, based on he presence of a particular frequency range of brain activity in the frontal lobes, which are typically associated with various emotions, the media guidance application may (e.g., via monitoring component 316 (FIG. 3)) determine that a user is happy.

At step 1306, the media guidance application cross-references the first region with a database associated with functions performed by the user using regions of the brain to determine at least one function the user is performing based on the brain activity of the user in the first region of the brain. For example, in response to detecting (e.g., via monitoring component 316 (FIG. 3)) the first brain state in a particular region (e.g., portion 502, 504, 506, and/or 508 (FIG. 5)) of the brain (e.g., brain 510 (FIG. 5)) of a user (e.g., user 500 (FIG. 5)), the media guidance application may cross-reference a database to determine the functions that are typically associated with that region of the brain.

For example, in response to detecting brain activity in the parietal lobe, the media guidance application may (e.g., via control circuitry 304 (FIG. 4)) access a database (e.g., located locally at storage 308 (FIG. 3) or remotely at any location accessible via communications network 414 (FIG. 4)) listing functions of the parietal lobe. In response the media guidance application may receive a particular function or a list of functions that the user may be performing based on the brain activity in the parietal lobe. For example, the media guidance application may (e.g., via processing circuitry 306 (FIG. 3)) determine that the user is either reading or performing mathematical calculations.

In some embodiments, the media guidance application may further filter the possible functions that a user is performing by analyzing the content a user is consuming (e.g., on a display 312 (FIG. 3)). For example, in some embodiments, the media guidance application may receive information (e.g., as metadata) describing the current content that a user is consuming. Alternatively or additionally, the media guidance application may incorporate or have access to one or more content-recognition modules, which may be used by the media guidance application to analyze media objects and/or the content of media objects. For example, the media guidance application may include an object recognition module. The object recognition module may use edge detection, pattern recognition, including, but not limited to, self-learning systems (e.g., neural networks), optical character recognition, on-line character recognition (including, but not limited to, dynamic character recognition, real-time character recognition, intelligent character recognition), and/or any other suitable technique or method to determine the objects in and/or characteristics of video and audio content. For example, the media guidance application may receive a media asset in the form of a video (e.g., an audio/video recording of a user). The video may include a series of frames. For each frame of the video, the media guidance application may use an object recognition module to determine the content and context of a media asset for use in determining the functions that a user may be performing.

In some embodiments, the content-recognition module or algorithm may also include audio analysis and speech recognition techniques, including, but not limited to, Hidden Markov Models, dynamic time warping, and/or neural networks (as described above) to process audio data and/or translate spoken words into text or other data forms that may be processed by the media guidance application. The content-recognition module may also use any other suitable techniques for processing audio and/or visual data. For example, the content-recognition module may analyze audio data to determine the content and context of a media asset.

In some embodiments, attributes of media content or the asset information may indicate that a user is likely performing a particular function. For example, if possible functions include reading and performing mathematical computations, and the current content of the media asset the user is consuming includes text, but no numbers, the media guidance application may determine that the function the user is performing is reading and not number computations.

Upon determining the function a user is performing while consuming a media asset (e.g., on a display device such as user equipment device 402, 404, and/or 406 (FIG. 4)) the media guidance application determines (e.g., via processing circuitry 306 (FIG. 3)) whether or not the first brain state corresponds to a typical brain state of the user and/or all users performing the function. For example, if the brain state does not correspond (e.g., indicating that the user is straining), the media guidance application may (e.g., via control circuitry 304 (FIG. 3)) adjust the media asset.

At step 1308, the media guidance application compares the first brain state to a threshold range for preforming the at least one function. For example, the media guidance application may (e.g., via processing circuitry 306 (FIG. 3)) determine the particular frequency range, frequency band, electrical activity, etc. associated with the first brain state and compare that information to the frequency range.

At step 1310, in response to determining the first brain state does not correspond to the threshold range, the media guidance application may perform a media guidance application operation associated with the at least on function. For example, the media guidance application may detect a first brain state associated with the occipital lobe (e.g., occipital lobe 516 (FIG. 5)) of the user. In response to determining that the occipital lobe is associated with vision, the media guidance application may compare the first brain state of the user to a typical brain state of the user (e.g., retrieved from a user profile) associated with viewing media assets (e.g., represented by a threshold range). In response to determining that the brain state of the user does not correspond to the typical brain state (e.g., indicating that the user is having difficulty seeing the media assets, the user is squinting, the media asset is too bright, etc.), the media guidance application may modify (e.g., increase the size of text on the display device, reduce a brightness setting of the display device, etc.) the media assets, display settings, etc. in order to align the brain state of the user with the typical brain state.

In another example, the media guidance application may detect a state of the brain activity associated with various regions of the brain in order to perform a function. For example, the media guidance application may detect a state of the brain activity associated with the occipital lobe (e.g., associated with vision) and the parietal lobe (e.g., associated with reading) of the user. In response to determining that the brain state of the brain activity associated with the occipital lobe (e.g., associated with vision) and the parietal lobe (e.g., associated with reading) of the user does not correspond to the typical brain state of a user, while the temporal lobe (e.g., associated with hearing) does correspond to the typical brain state of the user (e.g., indicating that user is straining to read and/or see a media asset, but not straining to hear a media asset), the media guidance application may modify the media assets, display settings, etc. such that text or important events are communicated to the user via verbal means (e.g., audio announcements).

It is contemplated that the steps or descriptions of FIG. 13 may be used with any other embodiment of this disclosure. In addition, the steps and descriptions described in relation to FIG. 13 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one or more of the steps in FIG. 13.

FIG. 14 is a flow-chart of illustrative steps involved in determining a function associated with particular brain activity. It should be noted that process 1400 or any step thereof, could be displayed on, or provided by, any of the devices shown in FIGS. 3-4 and 6 in response to brain activity of a user (e.g., user 500 (FIG. 5)). For example, process 1400 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1400 may be incorporated into or combined with one or more steps of any other process (e.g. as described in FIGS. 7-13 and 15-18).

At step 1402, the media guidance application receives information on a brain state of a region of a brain of a user. For example, in some embodiments, step 1402 may correspond to step 1302 (FIG. 13). For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a region (e.g., portion 502, 504, 506, and/or 508 (FIG. 5)) of a brain (e.g., brain 510 (FIG. 5)) of a user (e.g., user 500 (FIG. 5)).

At step 1404, the media guidance application retrieves a list of functions performed using the region of the brain of the user. For example, in response to detecting brain activity in the occipital lobe (e.g., occipital lobe 516 (FIG. 5)), the media guidance application may (e.g., via control circuitry 304 (FIG. 4)) access a database (e.g., located locally at storage 308 (FIG. 3) or remotely at any location accessible via communications network 414 (FIG. 4)) listing functions of the occipital lobe. In response the media guidance application may receive a particular function or a list of functions that the user may be performing based on the brain activity in the occipital lobe. For example, the media guidance application may (e.g., via processing circuitry 306 (FIG. 3)) determine that the occipital lobe is associated with visual perception and color perception based on a list received (e.g., via I/O path 302 (FIG. 3)) from the database.

At step 1406, the media guidance application selects a function from the list of functions. For example, if the list includes multiple functions that may be being performed, the media guidance application (e.g., via processing circuitry 306 (FIG. 3)) selects the first function in the list. At step 1408, the media guidance application determines whether or not the selected function corresponds to current activity of the user. For example, if the media guidance application determines that a current media asset (e.g., presented on user equipment 402, 404, and/or 406 (FIG. 4)) includes color (e.g., via metadata associated with the media asset and/or the object recognition techniques discussed above), the media guidance application may (e.g., via processing circuitry 306 (FIG. 3)) determine that a selected function of color perception does correspond to the current activity of the user. If so, the media guidance application proceeds to step 1410. Alternatively, if the media guidance application determines that a current media asset (e.g., presented on user equipment 402, 404, and/or 406 (FIG. 4)) does not include color (e.g., the media asset is consumed in black and white), the media guidance application may (e.g., via processing circuitry 306 (FIG. 3)) determine that a selected function of color perception does not correspond to the current activity of the user. If so, the media guidance application returns to step 1406 and selects a different function from the list of functions.

At step 1410, the media guidance application retrieves a threshold range of brain activity associated with the function. For example, the threshold range may indicate the typical brain activity associated with performing the selected function. In some embodiments, this step may correspond to step 1306 (FIG. 13)). It should be noted that in some embodiments, the media guidance application may determine (e.g., via processing circuitry 306 (FIG. 3)) that multiple functions correspond to the current activity of the user. In such cases, the media guidance application may retrieve composite threshold ranges, which account for multiple functions being performed by a user.

At step 1412, the media guidance application determines whether or not the brain state corresponds to the threshold range. For example, the media guidance application may (e.g., via processing circuitry 306 (FIG. 3)) compare the frequency range, frequency bands, electrical activity, etc. of the brain state to the threshold range. If the brain state corresponds to the threshold range (e.g., if the brain state matches the threshold range within an acceptable deviation), the media guidance application returns to step 1402. If the media guidance application determines that the brain state does not correspond to the threshold range, the media guidance application proceeds to step 1414.

At step 1414, the media guidance application performs a media guidance application operation corresponding to the function. For example, the media guidance application may cross-reference the function and the brain state of the user with a database (e.g., located locally on storage 308 (FIG. 3) or remotely at any location accessible via communications network 414 (FIG. 4)) in order to determine a particular media guidance application operation that may align the brain state of the user with the threshold range.

For example, if the user is having trouble seeing (e.g., as indicated by brain activity indicative of straining) the media guidance application may generate on screen text in a larger size. In another example, if a user does not have brain activity corresponding to a particular function (e.g., vision) indicating the user has a deficiency related to that particular function (e.g., is blind), the media guidance application may determine another function (e.g., hearing) associated with a different region of the brain (e.g., temporal lobe) and modify the media asset (e.g., generate audio announcements of subtitles) such that that region of the brain is used by a user to consume the media asset.

At step 1416, the media guidance application receives updated information on the brain state. For example, the media guidance application (e.g., implemented on user device 300 (FIG. 3)) may receive new data (e.g., from monitoring component 316 (FIG. 3)) associated with the brain activity (e.g., the current frequency range of voltage fluctuations in the brain and/or electrical activity of muscles near the brain at rest and during contraction) of a region (e.g., portion 502, 504, 506, and/or 508 (FIG. 5)) of a brain (e.g., brain 510 (FIG. 5)) of a user (e.g., user 500 (FIG. 5)) in order to determine whether or not modifying the media asset was successful in aligning the brain state of the user with the threshold range. The media guidance application then returns to step 1412.

It is contemplated that the steps or descriptions of FIG. 14 may be used with any other embodiment of this disclosure. In addition, the steps and descriptions described in relation to FIG. 14 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 14.

FIG. 15 is a flow-chart of illustrative steps involved in changing a user device from one mode to another based on brain activity. It should be noted that process 1500 or any step thereof, could be provided by, any of the devices shown in FIGS. 3-4 and 6 in response to brain activity of a user (e.g., user 500 (FIG. 5)). For example, process 1500 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1500 may be incorporated into or combined with one or more steps of any other process (e.g. as described in FIGS. 7-14 and 18).

In some embodiments, the media guidance application (or a user device upon which the media guidance application is implemented) may manage power consumption of the user device based on brain activity of a user. For example, the media guidance application may operate in a plurality of modes each associated with a power consumption and/or sensitivity level.

At step 1502, the media guidance application receives a user request to monitor brain activity of a user with a user device, in which the user device operates in a first mode and a second mode, and wherein the first mode is associated with a first power consumption level and the second mode is associated with a second power consumption level. For example, the media guidance application may receiving a user input (e.g., via user input interface 310 (FIG. 3)) requesting that a user device (e.g., user device 600, 630, and/or 660 (FIG. 6)) operate in a first mode or a second mode.

At step 1504, the media guidance application, in response to the user request, monitors the brain activity of the user with the user device in the first mode. For example, the media guidance application may receive a user selection (e.g., of selectable option 204 (FIG. 2)), initiating the monitoring the user's brain activity. Upon initiation, the media guidance application may operate in a first mode (e.g., as determined by PMU 318 (FIG. 3)).

At step 1506, the media guidance application, in response to detecting the brain activity of the user does not correspond to a threshold range, changes from the first mode to the second mode and monitors the brain activity of the user with the user device in the second mode.

For example, the media guidance application (or a user device upon which the media guidance application is implemented) may include a "sleep mode" (e.g., a lower powered/lower sensitivity mode) that is initiated after prolong periods of similar brain activity and/or repetitive brain activity cycles. For example, the media guidance application may initiate the sleep mode in response to determining that the brain activity of the user has dropped below a first threshold range (e.g., associated with an awake user). In another example, the media guidance application may detect that the brain activity of the user exceeds a second threshold range (e.g., associated with a sleeping user), and in response, initiate an "active mode."

It is contemplated that the steps or descriptions of FIG. 15 may be used with any other embodiment of this disclosure. In addition, the steps and descriptions described in relation to FIG. 15 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 15.

Figure 16:
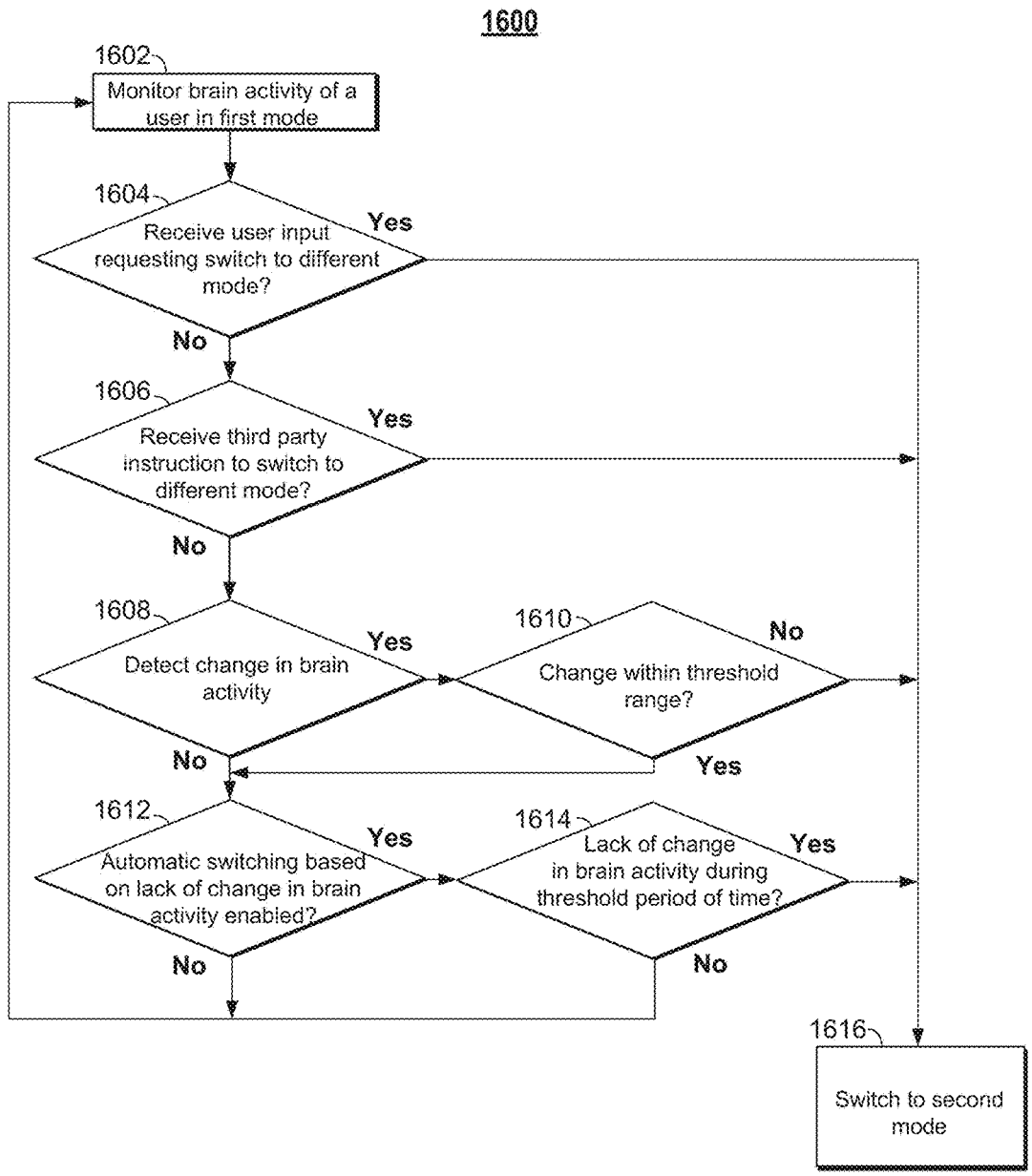
FIG. 16 is a flow-chart of illustrative steps involved in determining when to change a user device from one mode to another based on brain activity in accordance with some embodiments of the disclosure.

FIG. 16 is a flow-chart of illustrative steps involved in determining when to change a user device from one mode to another based on brain activity. It should be noted that process 1600 or any step thereof, could be provided by, any of the devices shown in FIGS. 3-4 and 6 in response to brain activity of a user (e.g., user 500 (FIG. 5)). For example, process 1600 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1600 may be incorporated into or combined with one or more steps of any other process (e.g. as described in FIGS. 7-15, 17 and 18).

At step 1602, the media guidance application monitors brain activity of a user in a first mode. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5)) based on a power consumption and/or sensitivity level of the first mode.

At step 1604, the media guidance application determines whether or not a user input requesting a switch to a different mode is received. For example, the media guidance application may receive various inputs (e.g., via user input interface 310 (FIG. 3)) from a user. The media guidance application may receive a request from a user to lower a current power consumption and/or sensitivity level of a user device (e.g., user device 600, 630, and/or 660 (FIG. 6)) in order to extend the life of an energy storage device or limit the exposure of a user (e.g., user 500 (FIG. 5)) to activities of the monitoring component. Alternatively, the media guidance application may receive a request from a user to increase a current power consumption and/or sensitivity level of a user device (e.g., user device 600, 630, and/or 660 (FIG. 6)) in order to generate more accurate results and/or monitor a particular region of the brain.

If the media guidance application receives a user input request to switch to a different mode, the media guidance application proceeds to step 1616. If the media guidance application does not receive a user request to switch to a different mode, the media guidance application proceeds to step 1606.

At step 1606, the media guidance application determines whether or not a third party instruction to switch to a different mode is received. For example, the media guidance application (e.g., implemented in user device 600, 630, and/or 660 (FIG. 6)) may receive instructions (e.g., via I/O path 302 (FIG. 3)) for particular modes the user device configured. For example, a remote source (e.g., media guidance data source 418 (FIG. 4)) may determine the particular brain activity and/or regions of the brain that should be monitored. In such cases, the media guidance application may need to operate in a particular mode.

If the media guidance application receives a third party instruction to switch to a different mode, the media guidance application proceeds to step 1616. If the media guidance application does not receive a third party instruction to switch to a different mode, the media guidance application proceeds to step 1608.

At step 1608, the media guidance application determines whether or not a change in the brain activity is detected. For example, the media guidance application may detect a change (e.g., via monitoring component 316 (FIG. 3)). If the media guidance application does not detect a change, the media guidance application proceeds to step 1612. If the media guidance application determines a change was detected, the media guidance application proceeds to step 1610 and determines if the change was within the threshold range. For example, in some embodiments, the media guidance application may allow for transient variations and amplitudes as long as the variations and amplitudes are within a threshold range. If the change is not within the threshold range, the media guidance application proceeds to step 1616. If the change is within the threshold range, the media guidance application proceeds to step 1612.

At step 1612, the media guidance application determines whether or not to automatically switch based on a lack of change in brain activity is enabled. For example, a user may enable automatic switching based on a lack of change in brain activity (e.g., via user input interface 310 (FIG. 3)) in order to extend the life of an energy storage device or limit the exposure of a user (e.g., user 500 (FIG. 5)) to the activities of a monitoring component (e.g., monitoring component 316 (FIG. 3)). For example, a user may request the media guidance application to engage a "sleep" mode after determining that a user has maintained a particular threshold range for a particular amount of time. For example, a user may be sleeping, consuming a feature length media asset, and/or performing another activity that does not require media guidance. If automatic switching is not enabled, the media guidance application returns to step 1602. If automatic switching is enabled, the media guidance application proceeds to step 1614.

At step 1614, the media guidance application determines whether or not there has been a lack of change in brain activity during a threshold period of time. For example, the media guidance application may automatically switch to a different mode, the media guidance application does not detect (e.g., via monitoring component 316 (FIG. 3)) a change in the brain activity of the user during a particular amount of time.

In some embodiments, the media guidance may select the particular amount of time constituting the threshold period of time based on instructions received from storage 308 (FIG. 3). Alternatively or additionally, the media guidance application (e.g., implemented on user device 300 (FIG. 3)) may receive instructions from a remote source (e.g., any location accessible via communications network 414 (FIG. 4)). The media guidance application may also receive a user input (e.g., via user input interface 310 (FIG. 3)) customizing the threshold period of time. If the media guidance application determines that there has been a change in brain activity within the threshold period of time, the media guidance application returns to step 1602. If the media guidance application determines that there has not been a change within the threshold period of time, the media guidance application proceeds to step 1616 and switches to a second mode.

It is contemplated that the steps or descriptions of FIG. 16 may be used with any other embodiment of this disclosure. In addition, the steps and descriptions described in relation to FIG. 16 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 16.

Figure 17:
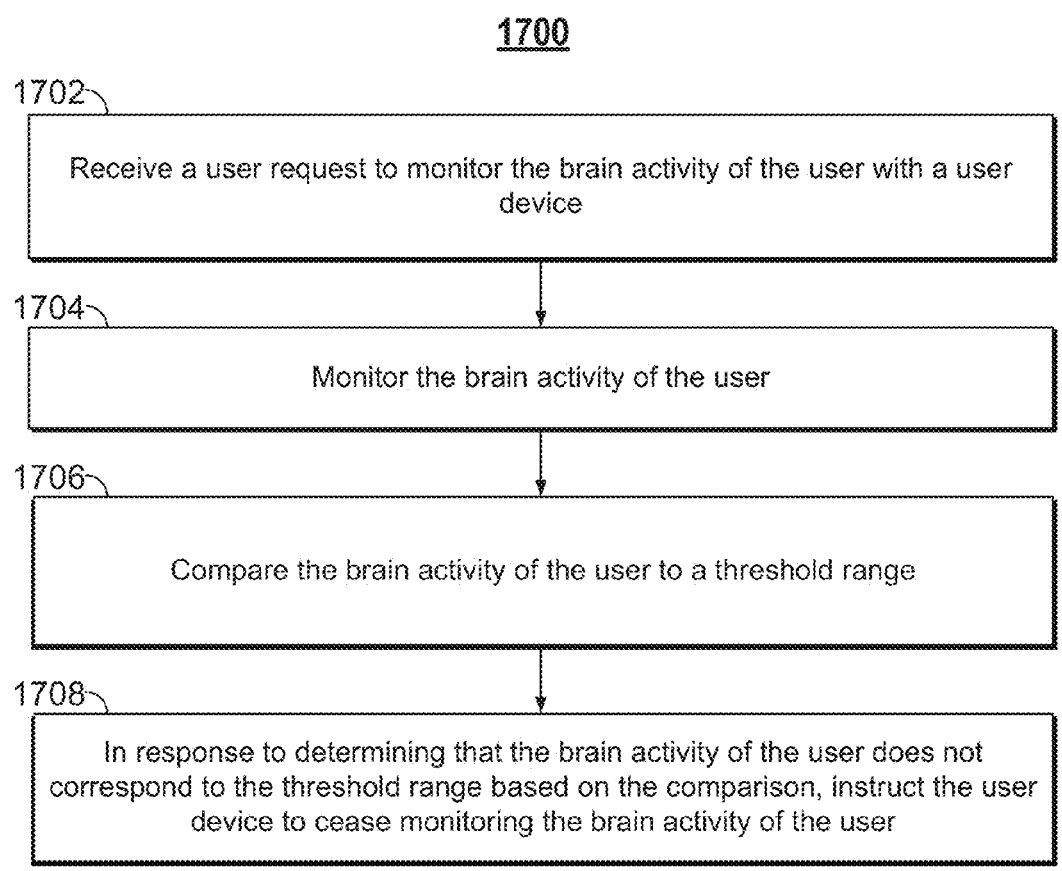
FIG. 17 is a flow-chart of illustrative steps involved in halting the monitoring of brain activity in based on brain activity of a user accordance with some embodiments of the disclosure.

FIG. 17 is a flow-chart of illustrative steps involved in halting the monitoring of brain activity in based on brain activity of a user. It should be noted that process 1700 or any step thereof could be provided by any of the devices shown in FIGS. 3-4 and 6 in response to brain activity of a user (e.g., user 500 (FIG. 5)). For example, process 1700 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1700 may be incorporated into or combined with one or more steps of any other process (e.g. as described in FIGS. 7-16 and 18).

At step 1702, the media guidance application receives a user request to monitor the brain activity of the user with a user device. For example, in some embodiments, the media guidance application may perform various media guidance application operations (e.g., as discussed above) based on a user achieving (or varying from) a particular brain state. In order to enable performing the various media guidance operations based on the brain activity of the user, the media guidance application may first need to be activated.

In some embodiments, the media guidance application may receive a user input (e.g., via user input interface 310 (FIG. 3)) indicating that the user would like to initiate brain activity monitoring. In some embodiments, the user input may power on the user device, and/or in some embodiments, the user input may adjust the mode of the user device (e.g., as discussed above).

At step 1704, the media guidance application monitors the brain activity of the user. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5))).

In some embodiments, the media guidance application may continuously monitor the brain activity of a user using an EEG, EMG, or a suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input (e.g., selecting selectable option 204 (FIG. 2)).

At step 1706, the media guidance application compares the brain activity of the user to a threshold range. For example, the media guidance application may retrieve a threshold range, which if detected causes the media guidance application to issue instructions (e.g., via control circuitry 304 (FIG. 3)) to perform one or more actions (e.g., powering off the user device, adjusting the current mode of the user device, performing a media guidance application operation, etc.).

In some embodiments, the threshold range may depend on the user (e.g., based on information in a user profile), and/or may be based on the particular action to be performed (e.g., each media guidance application operation may be associated with a unique threshold range), based on information received from a remote (e.g., an industry standard threshold range) or local source (e.g., storage 308 (FIG. 3)), etc.

To compare the brain activity of the user to the threshold range, the media guidance application may first identify a brain state corresponding to the brain activity of the user. The brain state may correspond to the average frequencies and amplitudes of brain waves in the brain of a user. For example, a brain state may be associated with the average frequencies and amplitudes of brain activity of a user over a period of time (e.g., 5 seconds). For example, if the threshold range over the period of time includes an average frequency of 4 Hz and an amplitude of 15 microvolts (e.g., as determined by processing circuitry 306 (FIG. 3)), and the brain activity of the user averages a frequency of 5 Hz and/or 10 microvolts over the period of time, the media guidance application may determine that the brain activity and/or brain state does not correspond to the threshold range. In another example, the threshold range may be associated with frequencies between 3-5 Hz and amplitudes of between 10-20 microvolts. In response to determining that the brain activity of a user does not have frequencies between 3-5 Hz and/or amplitudes between 10-20 microvolts (e.g., as determined by processing circuitry 306 (FIG. 3)), the media guidance application may determine that the brain activity and/or brain state does not correspond to a threshold range.

Figure 19:
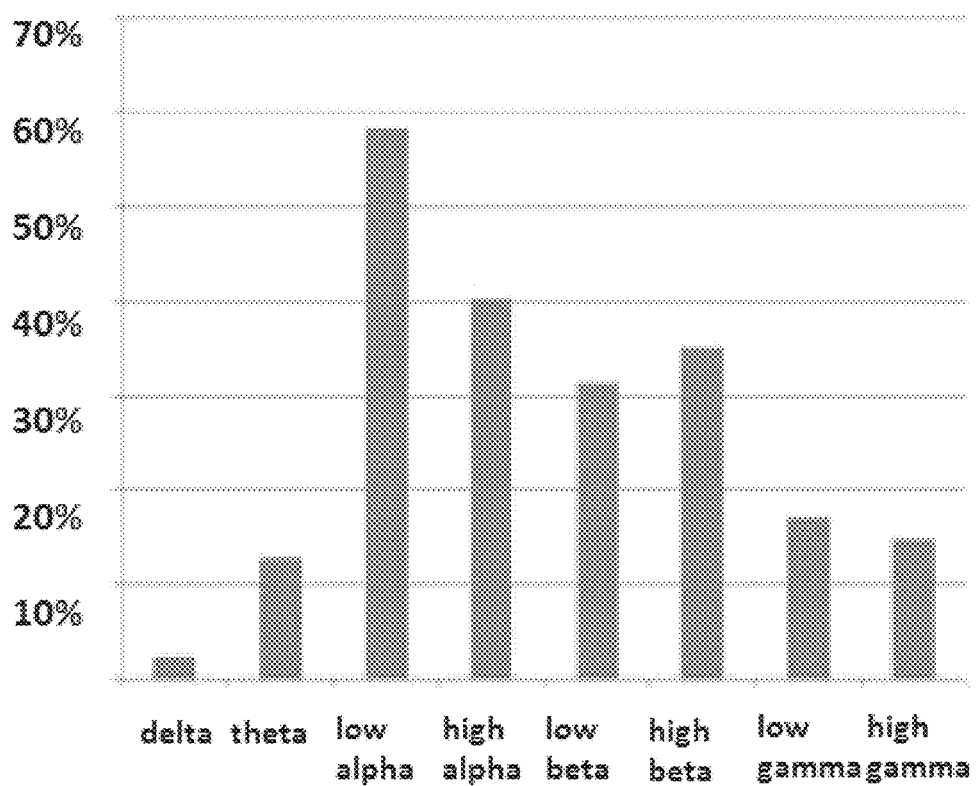
FIG. 19 is a table that shows a percent decrease in the amplitudes of various frequency bands one minute after a user closed his eyes and began resting.

For example, as shown in FIG. 19 below, within minutes of a user falling asleep the brain activity of the user (e.g., the amplitudes associated with different frequencies) may decrease dramatically. FIG. 10 shows a percent decrease in the amplitudes of various frequency bands one minute after a user closed his eyes and began resting. As shown in FIG. 19 above, certain frequency bands may experience dramatic changes as a user engages in different behaviors. Accordingly, the media guidance application (e.g., via monitoring component 316 (FIG. 3)) may detect these changes and compare the changes (or the brain activity after the changes) to the threshold range). For example, as a user falls asleep, the media guidance application may determine that the brain activity of the user no longer corresponds to a threshold range associated with a user being awake.

In another example, an EMG (e.g., incorporated into a monitoring component 316 (FIG. 3)) may determine that the muscles near the brain (e.g., associated with the blinking of the eyes) showed a decrease of eye blinks from every two or three seconds to about one blink per minute. In such cases, the threshold range may be expressed in terms of electrical activity in the muscles near the brain and/or the number of eye blinks over a particular period of time.

At step 1708, the media guidance application in response to determining that the brain activity of the user does not correspond to the threshold range based on the comparison, instructs the user device to cease monitoring the brain activity of the user. For example, the media guidance application may trigger (e.g., via control circuitry 304 (FIG. 3)) various modes for monitoring brain activity, in which each mode is associated with a different power consumption level and/or sensitivity level (e.g., as discussed above with regard to FIGS. 15-16). One such mode may correspond to the user device (e.g., user device 300 (FIG. 3)) being powered-off. For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) in order to extend the life of an energy storage device or limit the exposure of a user (e.g., user 500 (FIG. 5)) to activities of the monitoring component. In some embodiments, the power consumption and/or sensitivity level may be associated with being monitored for a particular brain state. For example, if monitoring of the particular brain state requires a lower (or no) degree of sensitivity, the media guidance application (e.g., via control circuitry 304 (FIG. 3)) may instruct PMU 318 (FIG. 3) to switch to a mode corresponding to a lower level of sensitivity and/or power consumption level.

It is contemplated that the steps or descriptions of FIG. 17 may be used with any other embodiment of this disclosure. In addition, the steps and descriptions described in relation to FIG. 17 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 17.

Figure 18:
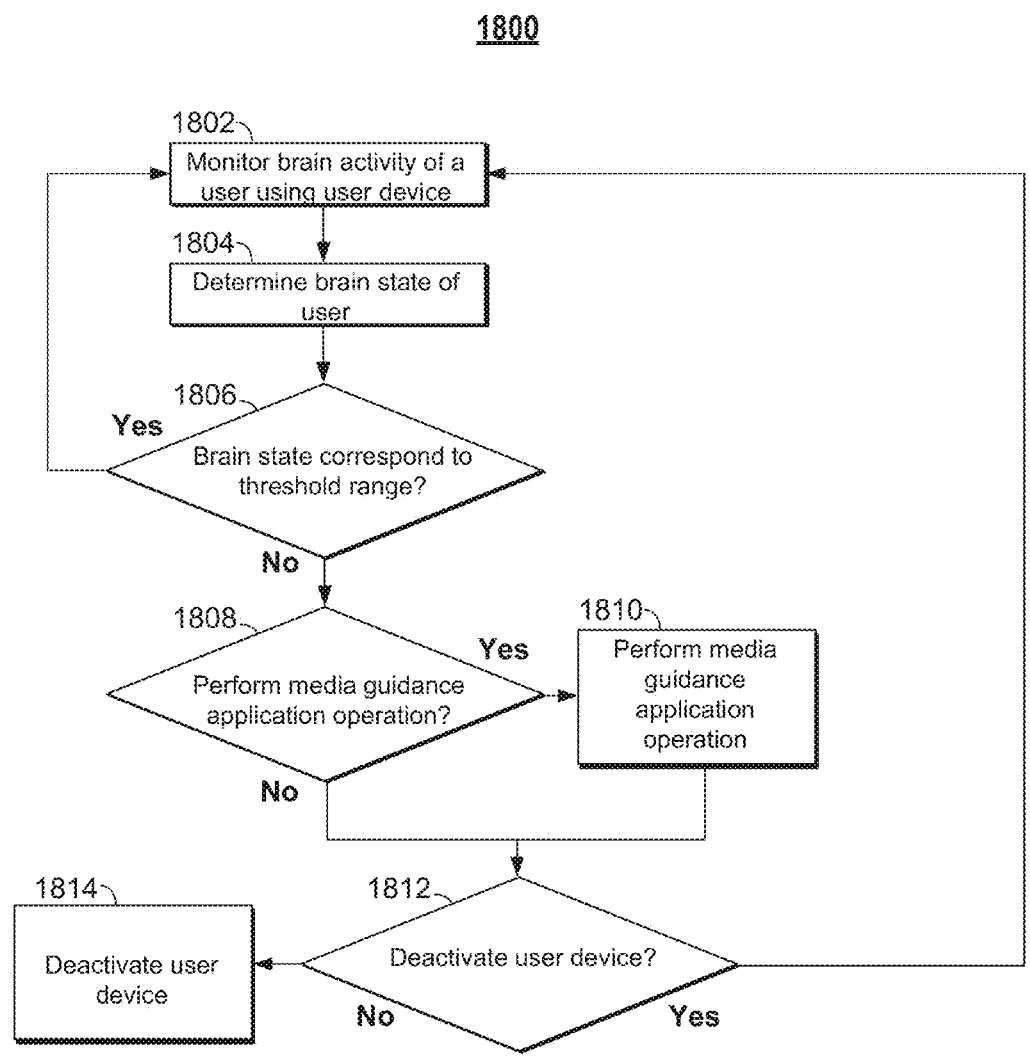
FIG. 18 is a flow-chart of illustrative steps involved in performing a media guidance application operation based on brain activity of a user in accordance with some embodiments of the disclosure.

FIG. 18 is a flow-chart of illustrative steps involved in performing a media guidance application operation based on brain activity of a user. It should be noted that process 1800 or any step thereof could be provided by any of the devices shown in FIGS. 3-4 and 6 in response to brain activity of a user (e.g., user 500 (FIG. 5)). For example, process 1800 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 1800 may be incorporated into or combined with one or more steps of any other process (e.g. as described in FIGS. 7-17).

It is contemplated that the steps or descriptions of FIG. 18 may be used with any other embodiment of this disclosure. In addition, the steps and descriptions described in relation to FIG. 18 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 and 6 could be used to perform one of more of the steps in FIG. 18.

At step 1802, the media guidance application monitors the brain activity of a user using a user device. For example, in some embodiments, step 1802 may correspond to step 1704 (FIG. 17). For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles near the brain at rest and during contraction) of a user (e.g., user 500 (FIG. 5))).

At step 1804, the media guidance application determines a brain state of the user. For example, the media guidance application may receive data from a monitoring component (e.g., monitoring component 316 (FIG. 3)) incorporated into and/or in communication with (e.g., via communications network 414 (FIG. 4) a user device (e.g., user device 300

(FIG. 3) and/or user equipment device 402, 404, and/or 406 (FIG. 4)) upon which the media guidance application is implemented. The media guidance application may (e.g., via control circuitry 304 (FIG. 3)) process that data to determine a brain state that corresponds with the retrieved data. For example, the receiving data may correspond to a particular frequency range and/or electrical activity of the muscles near a particular region (e.g., frontal lobe 512 (FIG. 5)) of a brain (e.g., brain 510 (FIG. 5)) of the user.

At step 1806, the media guidance application determines whether or not the brain state corresponds to the threshold range. For example, in some embodiments, step 1806 may correspond to step 1706 (FIG. 17). To determine whether or not the brain state corresponds to the threshold range, the media guidance application (e.g., via processing circuitry 306 (FIG. 3)) may determine whether or not the bounds and/or values associated with the brain state are within the bounds and/or values associated with the threshold range.

If the media guidance application determines that the brain state does correspond to the threshold range, the media guidance application returns to step 1802. If the media guidance application determines that the brain state does not correspond to the threshold range, the media guidance application proceeds to step 1808.

At step 1808, the media guidance application determines whether or not to perform a media guidance application operation. For example, in some embodiments, the media guidance application may issue instructions (e.g., via control circuitry 304 (FIG. 3)) to perform one or more media guidance application operations (e.g., record and/or pause a currently presented media asset, lower the volume of a display device, etc.). For example, if the media guidance application determines that a user has fallen asleep (e.g., the brain state of a user no longer corresponds to the threshold range associate with an awake user), the media guidance application may record and/or pause the media asset. In another example, the media guidance application may additionally or alternatively lower the volume of the display device and/or set an alarm/reminder for when a user needs to wake up.

If the media guidance application determined to perform one or more media guidance application operations the media guidance application proceeds to step 1810 and performs the media guidance application before proceeding to step 1812. If the media guidance application determines not to perform the media guidance application operation the media guidance application proceeds to step 1812 without performing any media guidance application operation.

At step 1812, the media guidance application determines whether or not to deactivate the user device. For example, in some embodiments, the media guidance application may issue instructions (e.g., via control circuitry 304 (FIG. 3)) to power off the user device and/or change the user device to a different mode (e.g., corresponding to a different power consumption level). For example, if the media guidance application determines that a user has fallen asleep (e.g., the brain state of a user no longer corresponds to the threshold range associated with an awake user), the media guidance application may turn off the user device (e.g., user device 600, 630, and/or 660 (FIG. 6)).

If the media guidance application determines to deactivate the user device the media guidance application proceeds to step 1814 and deactivates the user device. If the media guidance application determines not to deactivate the user device, the media guidance application returns to step 1802. For example, the media guidance application may determine to adjust the power consumption level of the user device (e.g., as described in FIGS. 15-16) to a different mode rather that deactivate the user device.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real-time. It should also be noted, the systems and/or methods described above may be applied to, or used in accordance with, other systems and/or methods.

What is claimed is:

1. A method of performing an operation of a media guidance application in response to activity of a brain of a user, the method comprising:
   monitoring brain activity in a first region of the brain of the user, wherein the first region is associated with controlling eye blinking;
   detecting a first eye blink pattern of the user in the first region of the brain of the user, wherein the first eye blink pattern begins with an eye blink;
   in response to detecting the first eye blink pattern, initiating monitoring of brain activity in a second region of the brain of the user, wherein the second region is associated with an attentiveness level of the user;
   cross-referencing the brain activity associated with the attentiveness level of the user with a database associated with attentiveness levels and corresponding brain activity to determine the attentiveness level of the user;
   comparing the attentiveness level of the user to a threshold attentiveness level;
   determining, based on the comparing, that the user has a low attentiveness level when the attentiveness level of the user is below the threshold attentiveness level; and
   in response to determining that the user has the low attentiveness level, performing an operation that simultaneously executes a media guidance function and generates for display an icon on a display screen that provides feedback to the user related to the brain activity of the user and instructs the user to increase the attentiveness level of the user in order to halt execution of the media guidance function.

2. The method of claim 1, further comprising halting performance of the operation in response to detecting a second eye blink pattern.

3. The method of claim 1, wherein the first eye blink pattern comprises at least one eye blink.

4. The method of claim 1, wherein monitoring the brain activity of the user further comprises receiving data from an electroencephalogram unit indicating a first frequency range of the brain activity of the user or receiving data from an electromyogram unit indicating first electrical activity of muscles near the brain of the user at rest and during contraction.

5. The method of claim 4, wherein the electroencephalogram unit or the electromyogram unit is incorporated into a mobile headset, wherein the mobile headset is battery powered.

6. The method of claim 4, further comprising:
   cross-referencing the first frequency range of the brain activity of the user with a database associated with frequencies of brain states to determine the brain activity associated with an attentiveness level of the user or cross-referencing the first electrical activity of the muscles near the brain of the user with a database associated with electrical activity of brain states to determine the brain activity associated with an attentiveness level of the user.

7. The method of claim 1, wherein the operation further includes a navigation command, a fast-access playback command, a selection command, or a settings command.

8. The method of claim 1, further comprising generating for display a plurality of media listings in response to detecting the first eye blink pattern, wherein the operation includes navigating the plurality of media listings based on time or media provider.

9. The method of claim 8, further comprising selecting one of the plurality of media listings in response to determining the attentiveness level of the user satisfies the threshold attentiveness level while performing the operation.

10. A system of performing an operation of a media guidance application in response to activity of a brain of a user, the system comprising
user input circuitry; and
control circuitry configured to:
monitor brain activity in a first region of the brain of the user, wherein the first region is associated with controlling eye blinking;
detect, using the user input circuitry, a first eye blink pattern of the user in the first region of the brain of the user, wherein the first eye blink pattern begins with an eye blink;
in response to detecting the first eye blink pattern, initiate monitoring of brain activity in a second region of the brain of the user, wherein the second region is associated with an attentiveness level of the user;
cross-reference the brain activity associated with the attentiveness level of the user with a database associated with attentiveness levels and corresponding brain activity to determine the attentiveness level of the user;
compare the attentiveness level of the user to a threshold attentiveness level;
determine, based on the comparing, that the user has a low attentiveness level when the attentiveness level of the user is below the threshold attentiveness level; and
in response to determining that the user has the low attentiveness level, perform an operation that simultaneously executes a media guidance function and generates for display an icon on a display screen that provides feedback to the user related to the brain activity of the user and instructs the user to increase the attentiveness level of the user in order to halt execution of the media guidance function.

11. The system of claim 10, wherein the control circuitry is further configured to halt performance of the operation in response to detecting a second eye blink pattern.

12. The system of claim 10, wherein the first eye blink pattern comprises at least one eye blink.

13. The system of claim 10, wherein the control circuitry configured to monitor the brain activity of the user is further configured to receive data from an electroencephalogram unit indicating a first frequency range of the brain activity of the user or receive data from an electromyogram unit indicating first electrical activity of muscles near the brain of the user at rest and during contraction.

14. The system of claim 13, wherein the electroencephalogram unit or the electromyogram unit is incorporated into a mobile headset, wherein the mobile headset is battery powered.

15. The system of claim 13, wherein the control circuitry is further configured to:
cross-reference the first frequency range of the brain activity of the user with a database associated with frequencies of brain states to determine the brain activity associated with an attentiveness level of the user or cross-reference the first electrical activity of the muscles near the brain of the user with a database associated with electrical activity of brain states to determine the brain activity associated with an attentiveness level of the user.

16. The system of claim 10, wherein the operation further includes a navigation command, a fast-access playback command, a selection command, or a settings command.

17. The system of claim 10, wherein the control circuitry is further configured to generate for display a plurality of media listings in response to detecting the first eye blink pattern, wherein the operation includes navigating the plurality of media listings based on time or media provider.

18. The system of claim 17, wherein the control circuitry is further configured to select one of the plurality of media listings in response to determining the attentiveness level of the user satisfies the threshold attentiveness level while performing the operation.

* * * * *